(12) United States Patent
Wu et al.

(10) Patent No.: US 8,688,393 B2
(45) Date of Patent: Apr. 1, 2014

(54) TECHNIQUES FOR APPROXIMATING A DIFFERENCE BETWEEN TWO CAPACITANCES

(75) Inventors: Jin Yong Wu, Phoenix, AZ (US); Larry E. Tyler, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 585 days.

(21) Appl. No.: 12/846,650

(22) Filed: Jul. 29, 2010

(65) Prior Publication Data

US 2012/0024064 A1 Feb. 2, 2012

(51) Int. Cl.
*G01R 15/00* (2006.01)

(52) U.S. Cl.
USPC .................. 702/57; 324/679; 463/16

(58) Field of Classification Search
USPC ............................... 702/57, 73, 324
See application file for complete search history.

(56) References Cited

U.S. PATENT DOCUMENTS

| | | | | |
|---|---|---|---|---|
| 3,886,447 | A * | 5/1975 | Tanaka | 324/678 |
| 4,187,460 | A * | 2/1980 | Dauge et al. | 324/678 |
| 4,565,976 | A | 1/1986 | Campbell | |
| 4,621,227 | A * | 11/1986 | Venema | 324/678 |
| 4,709,225 | A | 11/1987 | Welland et al. | |
| 5,121,063 | A * | 6/1992 | Kerkow et al. | 324/601 |
| 5,465,604 | A * | 11/1995 | Sherman | 73/1.38 |
| 5,659,254 | A * | 8/1997 | Matsumoto et al. | 324/678 |
| 5,730,165 | A * | 3/1998 | Philipp | 137/1 |
| 5,777,482 | A * | 7/1998 | Tielert et al. | 324/678 |
| 5,974,895 | A | 11/1999 | Steger et al. | |
| 6,198,292 | B1 * | 3/2001 | Kirk et al. | 324/607 |
| 6,326,795 | B1 * | 12/2001 | Matsumoto et al. | 324/679 |
| 6,374,204 | B1 * | 4/2002 | Mandell et al. | 703/14 |
| 6,384,760 | B1 * | 5/2002 | Fuhrman | 341/128 |
| 6,424,276 | B1 * | 7/2002 | Munoz et al. | 341/120 |
| 6,433,713 | B1 * | 8/2002 | Fuhrman | 341/120 |
| 6,466,036 | B1 * | 10/2002 | Philipp | 324/678 |
| 6,586,943 | B1 * | 7/2003 | Masuda et al. | 324/500 |

(Continued)

FOREIGN PATENT DOCUMENTS

| | | |
|---|---|---|
| EP | 1879034 A1 | 1/2008 |
| GB | 2419950 A | 5/2006 |

OTHER PUBLICATIONS

International Search Report and Written Opinion of international application No. PCT/US2011/033926, dated Jul. 26, 2011, 13 pp.

(Continued)

*Primary Examiner* — Sujoy Kundu
*Assistant Examiner* — Alvaro Fortich
(74) *Attorney, Agent, or Firm* — Evans M. Mburu; Stephen W. Bauer

(57) ABSTRACT

A system includes a capacitance adjustment module and a control module. The capacitance adjustment module is configured to connect one or more of N capacitors in parallel with one of a first and second capacitance. The control module identifies the smaller of the first and second capacitances and identifies the larger of the first and second capacitances. Subsequently, the control module, during each of M iterations, instructs the capacitance adjustment module to connect at least one of the N capacitors across a set of nodes in parallel with the smaller identified capacitance, and determines whether the capacitance associated with the set of nodes is greater than the larger identified capacitance. After the M iterations, the control module approximates the difference between the first and second capacitances based on which of the N capacitors are connected across the nodes. M and N are integers greater than or equal to 1.

44 Claims, 23 Drawing Sheets

(56) References Cited

U.S. PATENT DOCUMENTS

| | | | |
|---|---|---|---|
| 6,657,444 B2* | 12/2003 | Fasen | 324/676 |
| 6,765,931 B1* | 7/2004 | Rabenko et al. | 370/493 |
| 6,777,956 B2* | 8/2004 | Davis | 324/658 |
| 6,949,937 B2 | 9/2005 | Knoedgen | |
| 7,403,020 B2* | 7/2008 | Braun et al. | 324/678 |
| 7,405,683 B1* | 7/2008 | Perrin et al. | 341/139 |
| 7,557,590 B2* | 7/2009 | Yakabe | 324/686 |
| 7,797,115 B2* | 9/2010 | Tasher et al. | 702/57 |
| 8,041,534 B2* | 10/2011 | Ogata et al. | 702/150 |
| 8,050,876 B2* | 11/2011 | Feen et al. | 702/57 |
| 8,207,882 B1* | 6/2012 | Jennings | 341/162 |
| 8,209,139 B2* | 6/2012 | Kuang | 702/65 |
| 8,289,034 B2* | 10/2012 | Kuang | 324/686 |
| 8,321,174 B1* | 11/2012 | Moyal et al. | 702/150 |
| 2001/0006371 A1* | 7/2001 | Bolz | 341/152 |
| 2002/0147555 A1* | 10/2002 | Nagata et al. | 702/70 |
| 2002/0169575 A1* | 11/2002 | Everitt | 702/107 |
| 2002/0175692 A1* | 11/2002 | Lasalandra et al. | 324/684 |
| 2003/0106372 A1 | 6/2003 | Adams et al. | |
| 2004/0160234 A1* | 8/2004 | Denen et al. | 324/679 |
| 2006/0238199 A1* | 10/2006 | Larsen | 324/329 |
| 2007/0046299 A1* | 3/2007 | Hargreaves et al. | 324/678 |
| 2007/0171107 A1* | 7/2007 | Wang | 341/143 |
| 2007/0227253 A1* | 10/2007 | Kleven | 73/718 |
| 2008/0042641 A1 | 2/2008 | Stockman | |
| 2008/0048679 A1* | 2/2008 | Hargreaves et al. | 324/678 |
| 2008/0048680 A1* | 2/2008 | Hargreaves et al. | 324/686 |
| 2008/0191713 A1* | 8/2008 | Hauer et al. | 324/658 |
| 2008/0204046 A1* | 8/2008 | Bartling | 324/658 |
| 2008/0297264 A1 | 12/2008 | Schwarz et al. | |
| 2009/0009194 A1* | 1/2009 | Seguine | 324/684 |
| 2009/0031809 A1 | 2/2009 | Lin et al. | |
| 2009/0039902 A1* | 2/2009 | Hargreaves et al. | 324/686 |
| 2009/0045822 A1* | 2/2009 | Nosovitsky et al. | 324/686 |
| 2009/0102935 A1* | 4/2009 | Hung et al. | 348/222.1 |
| 2009/0182534 A1* | 7/2009 | Loboz | 702/186 |
| 2009/0248335 A1* | 10/2009 | Elfadel et al. | 702/65 |
| 2009/0322351 A1* | 12/2009 | McLeod | 324/658 |
| 2010/0141275 A1* | 6/2010 | Matsushima | 324/678 |
| 2010/0148806 A1* | 6/2010 | Hargreaves et al. | 324/679 |
| 2010/0194408 A1* | 8/2010 | Sturmer et al. | 324/664 |
| 2010/0324841 A1* | 12/2010 | Tasher et al. | 702/57 |
| 2011/0025895 A1* | 2/2011 | Hasegawa | 348/294 |
| 2011/0193574 A1* | 8/2011 | De Boer et al. | 324/688 |
| 2011/0208457 A1* | 8/2011 | Merz et al. | 702/65 |
| 2011/0254565 A1* | 10/2011 | De Boer et al. | 324/601 |
| 2011/0273192 A1* | 11/2011 | Huang et al. | 324/678 |
| 2012/0084033 A1* | 4/2012 | Liu et al. | 702/65 |
| 2012/0228159 A1* | 9/2012 | Levine | 205/789 |

OTHER PUBLICATIONS

International Preliminary Report on Patentability for international application No. PCT/US2011/033926, dated Jul. 4, 2012, 16 pp.

Reply to Written Opinion dated Jul. 26, 2011, for international application No. PCT/US2011/033926, filed May 24, 2012, 12 pp.

Wu et al, "Servo Techniques for Approximation of Differential Capacitance of a Sensor ", U.S. Appl. No. 13/735,119, filed Jan. 7, 2013, 53 pages.

* cited by examiner

| Step | Control Module Instruction | Combined Capacitance | Comparision | Decision |
|---|---|---|---|---|
| Initial | 0000 | 0C + 3.5C | | |
| Iteration 1 | 1000 | 8C + 3.5C | 11.5C > 10C | Disconnect 8C cap. |
| Iteration 2 | 0100 | 4C + 3.5C | 7.5C < 10C | Do not disconnect 4C cap. |
| Iteration 3 | 0110 | 2C + 4C + 3.5C | 9.5C < 10C | Do not disconnect 2C cap. |
| Iteration 4 | 0111 | C + 2C + 4C + 3.5C | 10.5C > 10C | Addition of C inappropriate |
| Result | | | | $\Delta C_{approx} = 6C$ |

FIG. 9

| Step | Control Module Instruction | Combined Capacitance | Comparision | Decision |
|---|---|---|---|---|
| Initial | 10000 | 16C + 3.5C | 19.5C < 26C | Do not disconnect 16C cap. |
| Iteration 1 | 11000 | 16C + 8C + 3.5C | 27.5C > 26C | Disconnect 8C cap. |
| Iteration 2 | 10100 | 16C + 4C + 3.5C | 23.5C < 26C | Do not disconnect 4C cap. |
| Iteration 3 | 10110 | 16C + 4C + 2C + 3.5C | 25.5C < 26C | Do not disconnect 2C cap. |
| Iteration 4 | 10111 | 16C + 4C + 2C + 1C + 3.5C | 26.5C > 26C | Addition of C inappropriate |
| Result | | | | $\Delta C_{approx} = 6C$ |

FIG. 17

| Step | Control Module Instruction | Connected Capacitors | Comparision | Decision |
|---|---|---|---|---|
| Initial | 1000 | 8C | 8C < 10.5C | Do not disconnect 8C cap. |
| Iteration 1 | 1100 | 8C + 4C | 12C > 10.5C | Disconnect 4C cap. |
| Iteration 2 | 1010 | 8C + 2C | 10C < 10.5C | Do not disconnect 2C cap. |
| Iteration 3 | 1011 | 8C + 2C + C | 11C > 10.5C | Addition of C inappropriate |
| Result | | | | Target C = 10C |

FIG. 20

TECHNIQUES FOR APPROXIMATING A DIFFERENCE BETWEEN TWO CAPACITANCES

TECHNICAL FIELD

The disclosure relates to systems and methods for approximating capacitance, and, more particularly, to systems and methods for approximating a difference between two capacitances, which may be useful in capacitive sensors that may be implemented in, for example, medical devices.

BACKGROUND

Capacitive sensors may include one or more capacitors, the value of which indicates a sensed parameter. A detection circuit may measure values of capacitors included in a capacitive sensor to determine values of the sensed parameters indicated by the capacitive sensor. For example, a capacitive accelerometer may produce one or more capacitance values based on an acceleration experienced by the accelerometer. A detection circuit connected to the capacitive accelerometer may measure the one or more capacitance values and determine acceleration of the accelerometer based on the values.

In some implementations, accelerometers may include a sensing element that includes two parallel plate capacitors acting in a differential manner in which acceleration of the accelerometer causes one of the capacitors to increase in capacitance and the other capacitor to decrease in capacitance. At rest, or at a constant acceleration, the difference between capacitances in the accelerometer may remain constant. A detection circuit may determine the values of the capacitances in the accelerometer by applying a voltage to the capacitors, e.g., a square wave voltage, and producing an output voltage associated with the capacitors. The output voltage produced may be digitized using an analog to digital (A/D) converter in order to produce a digital value that indicates the amount and direction of acceleration that is suitable for use in digital systems. Typically, the detection circuit used for determining the digital values of the two capacitances may include amplifiers, filters, oscillators, A/D converters etc.

SUMMARY

In general, the disclosure is directed to systems and methods for approximating a difference between two capacitances. In one example, a capacitance approximation system according to the present disclosure determines an approximate difference in capacitance between a capacitance $C_1$ and a capacitance $C_2$. For example, $C_1$ and $C_2$ may be capacitances included in a capacitive sensor, such as an accelerometer, and accordingly, the capacitance approximation system may determine parameters measured by the capacitance based sensor, such as acceleration.

The capacitance approximation system determines the approximate difference in capacitance using an iterative approximation method according to the present disclosure. The iterative approximation method may include 3 phases. During the first phase, the capacitance approximation system determines which of $C_1$ and $C_2$ is smaller. The system may then modify the initially smaller of $C_1$ and $C_2$, as determined during the first phase, during subsequent phases.

The capacitance approximation system may include capacitance adjustment module having a set of N capacitors, each having predetermined values. During a series of iterations of the second phase, the system may connect various combinations of capacitors from the set of N capacitors in parallel with the initially smaller capacitance of $C_1$ and $C_2$. The system may determine, based on the iterations, which combination of the N capacitors best approximates the difference between $C_1$ and $C_2$. For example, the system may determine a maximum number of the N capacitors which may be connected in parallel with the initially smaller capacitance of $C_1$ and $C_2$ such that the combination of the capacitors and the initially smaller capacitance is not greater than the initially larger capacitance.

During the third phase, subsequent to the iterations, the system approximates the difference between $C_1$ and $C_2$ based on the combination of capacitors from the set of N capacitors that best approximates the difference between $C_1$ and $C_2$. For example, the system may determine that the approximate difference between $C_1$ and $C_2$ is equal to the sum of the combination of capacitors from the set of N capacitors that best approximates the difference between $C_1$ and $C_2$.

In one example, the present disclosure is directed to a system comprising a capacitance adjustment module and a control module. The capacitance adjustment module is configured to connect one or more of N capacitors in parallel with one of a first and second capacitance. The control module identifies the smaller of the first and second capacitances and identifies the larger of the first and second capacitances. Subsequently, the control module, during each of M iterations, instructs the capacitance adjustment module to connect at least one of the N capacitors across a set of nodes in parallel with the smaller identified capacitance, and determines whether the capacitance associated with the set of nodes is greater than the larger identified capacitance. After the M iterations, the control module approximates the difference between the first and second capacitances based on which of the N capacitors are connected across the nodes. M and N are integers greater than or equal to 1.

In another example, the present disclosure is directed to a method comprising identifying the smaller of a first capacitance and a second capacitance and identifying the larger of the first and second capacitances. The method further comprises, during each of M iterations, connecting at least one of N capacitors across a set of nodes in parallel with the smaller identified capacitance, determining whether the capacitance associated with the set of nodes is greater than the larger identified capacitance, and disconnecting the at least one of the N capacitors when the capacitance associated with the set of nodes is greater than the larger identified capacitance. Additionally, the method comprises, after the M iterations, approximating the difference between the first and second capacitances based on which of the N capacitors are connected across the set of nodes. M and N are integers greater than or equal to 1.

In another example, the present disclosure is directed to a system comprising means for identifying the smaller of a first capacitance and a second capacitance and means for identifying the larger of the first and second capacitances. The system further comprises means for, during each of M iterations, connecting at least one of N capacitors across a set of nodes in parallel with the smaller identified capacitance, determining whether the capacitance associated with the set of nodes is greater than the larger identified capacitance, and disconnecting the at least one of the N capacitors when the capacitance associated with the set of nodes is greater than the larger identified capacitance. Additionally, the system comprises means for, after the M iterations, approximating the difference between the first and second capacitances based on which of the N capacitors are connected across the set of nodes. M and N are integers greater than or equal to 1.

In another example, the present disclosure is directed to a system comprising a capacitance adjustment module and a control module. The capacitance adjustment module is configured to connect one or more of N capacitors in parallel with a first capacitance and configured to connect an offset capacitor having a predetermined value in parallel with a second capacitance. The control module, during each of M iterations, instructs the capacitance adjustment module to connect at least one of the N capacitors across a set of nodes in parallel with the first capacitance and determines whether the capacitance associated with the set of nodes is greater than the offset capacitor in parallel with the second capacitance. After the M iterations, the control module approximates the difference between the first and second capacitances based on which of the N capacitors are connected across the set of nodes. M and N are integers greater than or equal to 1.

In another example, the present disclosure is directed to a system comprising a capacitance adjustment module, a capacitance comparison module, and a control module. The capacitance adjustment module is configured to connect one or more of N capacitors across a set of nodes. The capacitance comparison module is configured to connect to the set of nodes, connect to a target capacitance, and determine which of the target capacitance and a capacitance associated with the set of nodes is larger. The control module, during each of M iterations, instructs the capacitance adjustment module to connect at least one of the N capacitors across the set of nodes, and instructs the capacitance comparison module to determine which of the target capacitance and the capacitance associated with the set of nodes is larger. After the M iterations, the control module approximates the target capacitance based on which of the N capacitors are connected across the set of nodes. M and N are integers greater than or equal to 1.

The details of one or more examples are set forth in the accompanying drawings and the description below. Other features, objects, and advantages will be apparent from the description and drawings, and from the claims.

BRIEF DESCRIPTION OF THE DRAWINGS

FIG. 9 is a table that illustrates a numerical example of the iterative approximation method.

FIG. 17 is a table that illustrates a numerical example of an iterative approximation method using the example capacitance approximation system of FIG. 16.

FIG. 20 is a table that illustrates a numerical example of an iterative approximation method using the example capacitance approximation system of FIG. 19.

DETAILED DESCRIPTION

Figure 1:
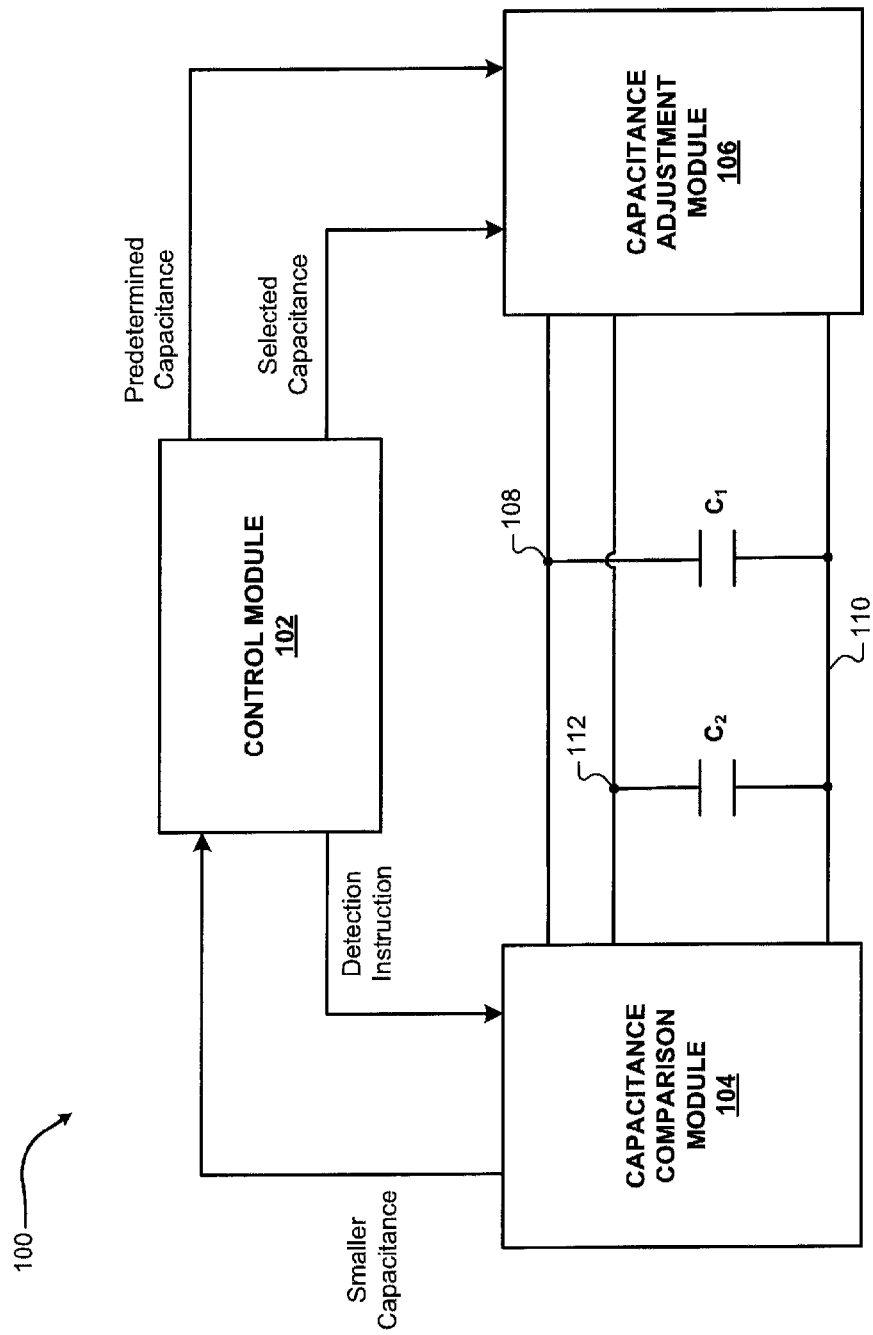
FIG. 1 is a functional block diagram of an example capacitance approximation system.

FIG. 1 is a functional block diagram of a capacitance approximation system 100 that determines an approximate difference in capacitance between capacitance $C_1$ and capacitance $C_2$. The capacitances $C_1$ and $C_2$, and the difference between $C_1$ and $C_2$, may be expressed in units of Farads (e.g., pico-farads).

Capacitance approximation system 100 includes a control module 102, a capacitance comparison module 104, and a capacitance adjustment module 106. The modules of the present disclosure, e.g., control module 102, capacitance comparison module 104, capacitance adjustment module 106, and other modules described herein may be implemented using electronic hardware, firmware, and/or software.

The modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Furthermore, the modules may comprise memory that may include computer-readable instructions that, when executed cause the modules to perform various functions attributed to the modules herein. Memory may include any volatile, non-volatile, magnetic, or electrical media, such as a random access memory (RAM), read-only memory (ROM), non-volatile RAM (NVRAM), electrically-erasable programmable ROM (EEPROM), flash memory, or any other digital media.

The modules of the present disclosure may also comprise any one or more of an application specific integrated circuit (ASIC), a microprocessor, a microcontroller, a digital signal processor (DSP), a field-programmable gate array (FPGA), or equivalent discrete or integrated logic circuitry. In some examples, modules may include multiple components, such as any combination of one or more microprocessors, one or more microcontrollers, one or more DSPs, one or more ASICs, or one or more FPGAs.

The functions attributed to the modules herein may be embodied as hardware, firmware, software, or any combination thereof. Depiction of different features as modules is intended to highlight different functional aspects and does not necessarily imply that such modules or units must be realized by separate hardware or software components. Rather, functionality associated with one or more modules may be performed by separate hardware or software components, or integrated within common or separate hardware or software components.

Throughout the disclosure, the actual difference between capacitances $C_1$ and $C_2$ may be referred to as $\Delta C$. Accordingly, capacitance approximation system 100 determines an approximate value of $\Delta C$. In other words, capacitance approximation system 100 approximates the actual difference between $C_1$ and $C_2$. Throughout the disclosure, the approximate value of $\Delta C$ determined by capacitance approximation system 100 may be referred to as $\Delta C_{approx}$.

$C_1$ and $C_2$ may represent any two capacitances in general, and accordingly, capacitance approximation system 100 may determine an approximate difference between any two capacitances. In one example, $C_1$ and $C_2$ may be included in a capacitance based sensor, such as an accelerometer. When $C_1$ and $C_2$ are included in an accelerometer, the difference between capacitances $C_1$ and $C_2$ may indicate an amount of acceleration experienced by the accelerometer, e.g., along a single axis in some accelerometers. Accordingly, when $C_1$ and $C_2$ are included in an accelerometer, capacitance approximation system 100 may be used to determine an approximate acceleration of the accelerometer. Although $C_1$ and $C_2$ may represent capacitances within a capacitance based accelerometer, the capacitances $C_1$ and $C_2$ may represent any two capacitances in other capacitance based sensors that indicate parameters other than acceleration.

Capacitance approximation system 100 determines $\Delta C_{approx}$ using an iterative approximation method. The iterative approximation method may include three phases. During the first phase, capacitance approximation system 100 determines which of $C_1$ and $C_2$ is smaller. Capacitance approximation system 100 may modify the smaller of $C_1$ and $C_2$, as determined during the first phase, during subsequent phases. In other words, the smaller of $C_1$ and $C_2$ may be selected by capacitance approximation system 100 for modification during subsequent phases of the iterative approximation method, and accordingly the smaller of $C_1$ and $C_2$ as determined during the first phase may be referred to as the "selected capacitance." The other capacitance (e.g., either $C_1$ or $C_2$), which is not selected for modification during the second and third phase may be referred to as the "unselected capacitance."

During the second phase of the iterative approximation method, capacitance approximation system 100 iteratively adds capacitances having different predetermined values in parallel with the selected capacitance. During each iteration, after a predetermined capacitance is added to the selected capacitance, capacitance approximation system 100 determines whether the selected capacitance in combination with the predetermined capacitance is greater than the unselected capacitance. During each iteration, subsequent to the determination, capacitance approximation system 100 either removes the predetermined capacitance (i.e., disconnects the predetermined capacitance from the selected capacitance) or maintains the connection between the predetermined capacitance and the selected capacitance for subsequent iterations. For example, capacitance approximation system 100 removes the predetermined capacitance if the combination of the selected capacitance and the predetermined capacitance is greater than the unselected capacitance. Alternatively, capacitance approximation system 100 maintains the connection between the predetermined capacitance and the selected capacitance for subsequent iterations if the combination of the selected capacitance and the predetermined capacitance is less than the unselected capacitance.

During subsequent iterations of the second phase, capacitance approximation system 100 adds capacitances having other predetermined values to the selected capacitance and determines whether each of the predetermined capacitances in combination with the selected capacitance is greater or less than the unselected capacitance. Additionally, during the subsequent iterations, capacitance approximation system 100 determines whether to disconnect or maintain the connection of the other predetermined capacitances to the selected capacitance.

During the third phase, after a plurality (e.g., 8) of iterations, capacitance approximation system 100 approximates the difference between the selected and unselected capacitances based on which predetermined capacitances are connected to selected capacitance. For example, capacitance approximation system 100 may determine that $\Delta C_{approx}$ is equal to the amount of capacitance that may be added to the selected capacitance without causing the sum of added capacitance and the selected capacitance to be greater than the unselected capacitance. In other words, capacitance approximation system 100 may determine that $\Delta C_{approx}$ is equal to a maximum amount of predetermined capacitance that may be added to the selected capacitance without causing the selected capacitance to increase to a value that is greater than the unselected capacitance.

Operation of control module 102, capacitance comparison module 104, and capacitance adjustment module 106 are now discussed. Control module 102 may instruct capacitance comparison module 104 and capacitance adjustment module 106, e.g., according to the iterative approximation method, in order to determine $\Delta C_{approx}$ (i.e., approximate $\Delta C$).

At the start of the iterative approximation method, control module 102 instructs capacitance comparison module 104 to determine which of $C_1$ and $C_2$ is smaller. This instruction from control module 102 is illustrated as "Detection Instruction" in FIG. 1. Capacitance comparison module 104, in response to the instruction from control module 102, determines which of $C_1$ and $C_2$ is smaller. Capacitance comparison module 104 then indicates to control module 102 which of $C_1$ and $C_2$ is smaller, illustrated as "Smaller Capacitance" in FIG. 1.

During subsequent steps of the iterative approximation method, control module 102 may modify whichever of $C_1$ and $C_2$ is initially determined to be smaller. The smaller of $C_1$ and $C_2$, as initially determined, may be subsequently adjusted according to the iterative approximation method, and may be referred to herein as the "selected capacitance." The larger of $C_1$ and $C_2$, as initially determined, may not be adjusted during the iterative approximation method, and may be referred to as the "unselected capacitance." Although the selected capacitance is described herein as being adjusted according to the iterative approximation method while the unselected capacitance is not adjusted, in other implementations, it is contemplated that either capacitance $C_1$ or $C_2$ may be modified during methods similar to the iterative approximation method as described herein. In one example, described with reference to FIGS. 14-15, the unselected capacitance may be modified to compensate for additional capacitance (e.g., parasitics) arising from operation of capacitance adjustment module 106.

After control module 102 receives indication of which of $C_1$ and $C_2$ is smaller, control module 102 may instruct capacitance adjustment module 106 to adjust the capacitance between the nodes 108 and 110 (i.e., nodes of $C_1$) and/or between nodes 112 and 110 (i.e., nodes of $C_2$). Instructions from control module 102 to capacitance adjustment module 106 may indicate where to add capacitance in the circuit, e.g., between nodes 108 and 110 or between nodes 112 and 110, and how much capacitance to add to the circuit. The instructions that indicate where to add capacitance and how much capacitance to add are illustrated in FIG. 1 as "Selected Capacitance" and "Predetermined Capacitance," respectively. Details regarding which of $C_1$ and $C_2$ is adjusted, and to what extend $C_1$ and $C_2$ are adjusted during the iterative approximation method are discussed hereinafter.

In one example, control module 102 may instruct capacitance adjustment module 106 to add capacitance in parallel with $C_1$, i.e., between nodes 108 and 110. In another example, control module 102 may instruct capacitance adjustment module 106 to add capacitance in parallel with $C_2$, i.e., between nodes 112 and 110. In still other examples, control module 102 may instruct capacitance adjustment module 106 to add capacitances to both $C_1$ and $C_2$.

Capacitance adjustment module 106 may adjust the capacitance between the nodes 108 and 110 of $C_1$ according to instructions from control module 102. For example, capacitance adjustment module 106 may add a capacitance in parallel with $C_1$ to increase capacitance between the nodes 108 and 110 of $C_1$ in response to instructions from control module 102. Hereinafter, adding capacitance between nodes 108 and 110 may be referred to as adjusting $C_1$ or adding capacitance to $C_1$, since adding capacitance between nodes 108 and 110 may be electrically equivalent to adjusting/adding capacitance to $C_1$.

Capacitance adjustment module 106 may adjust the capacitance between the nodes 112 and 110 of capacitance $C_2$ according to instructions from control module 102. For example, capacitance adjustment module 106 may add a capacitance in parallel with $C_2$ to increase capacitance between the nodes 112 and 110 of $C_2$. Hereinafter, adding capacitance between nodes 112 and 110 may be referred to as adjusting $C_2$ or adding capacitance to $C_2$, since adding capacitance between nodes 112 and 110 may be electrically equivalent to adjusting/adding capacitance to $C_2$.

In some implementations, as described herein, capacitance adjustment module 106 may include an array of capacitors in which each capacitor of the array has a predetermined capacitance. Accordingly, in some implementations, capacitance adjustment module 106 may add one or more capacitors of the array to either $C_1$ or $C_2$ to adjust the capacitance of $C_1$ or $C_2$, respectively, according to instructions from control module 102.

Figure 2:
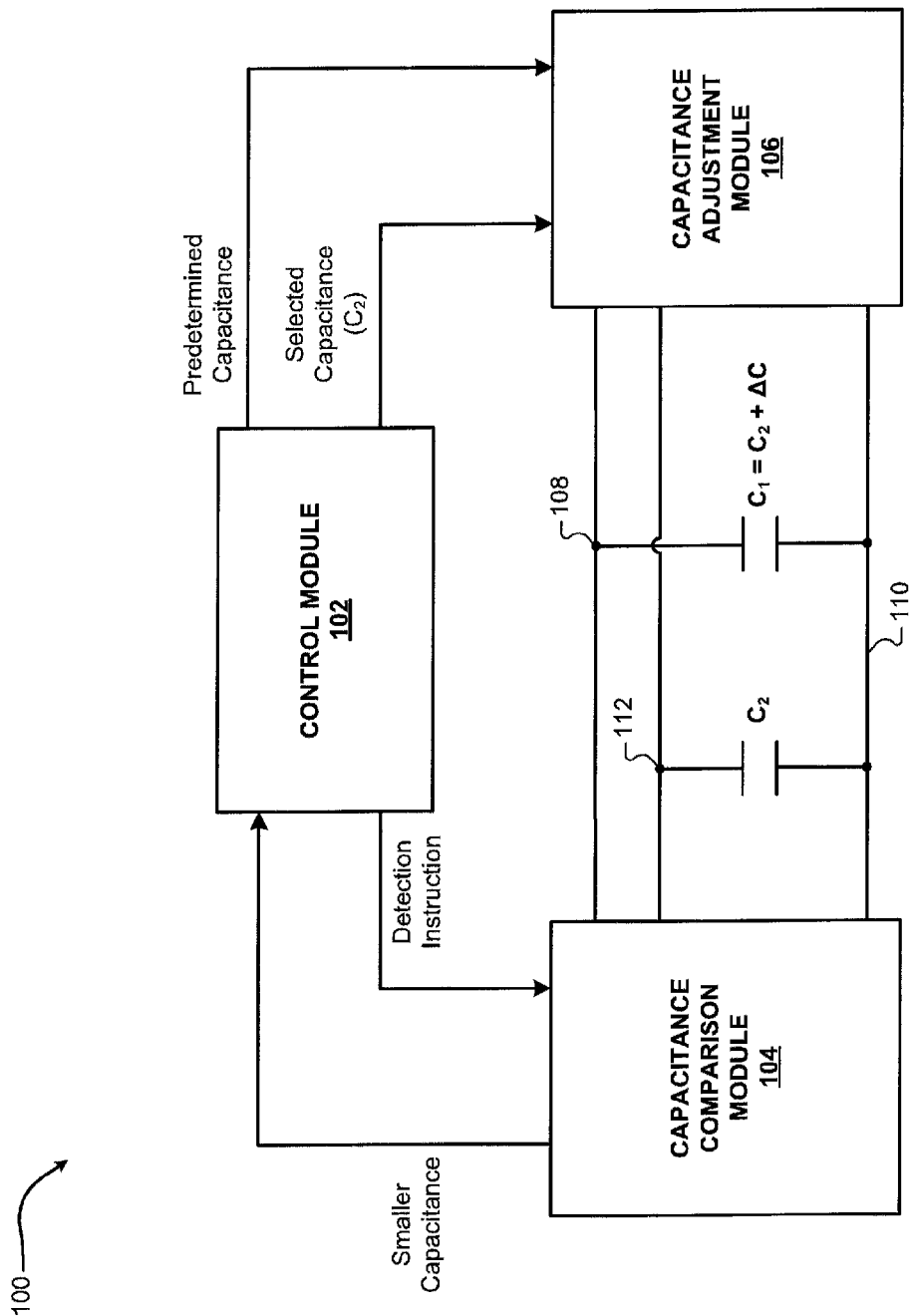
FIG. 2 is a functional block diagram of the example capacitance approximation system that illustrates relative values of $C_1$ and $C_2$.

Referring now to FIG. 2, in order to aid in the explanation of how capacitance approximation system 100 determines $\Delta C_{approx}$, it will be assumed hereinafter that $C_2$ is the smaller capacitance of $C_1$ and $C_2$. Accordingly, $C_1$ is illustrated in FIG. 2 as equal to $C_2$ plus an additional capacitance $\Delta C$ (i.e., the actual difference between $C_1$ and $C_2$). As illustrated in subsequent figures, capacitance approximation system 100 may be described as approximating $\Delta C$, i.e., determining $\Delta C_{approx}$, under the assumption that $C_1$ is equal to $C_2$ plus $\Delta C$.

As described above, capacitance approximation system 100 initially determines which of $C_1$ and $C_2$ is smaller. According to FIG. 2, control module 102 may instruct capacitance comparison module 104 to determine which of $C_1$ and $C_2$ is smaller, and in response to the instruction, capacitance comparison module 104 would determine that $C_2$ is smaller. Accordingly, control module 102 may select capacitance $C_2$ for adjustment during the iterative approximation method. Since $C_2$ is illustrated as the smaller capacitance, $C_2$ may also be referred to hereinafter as the selected capacitance and $C_1$ may be referred to as the unselected capacitance.

Figure 3:
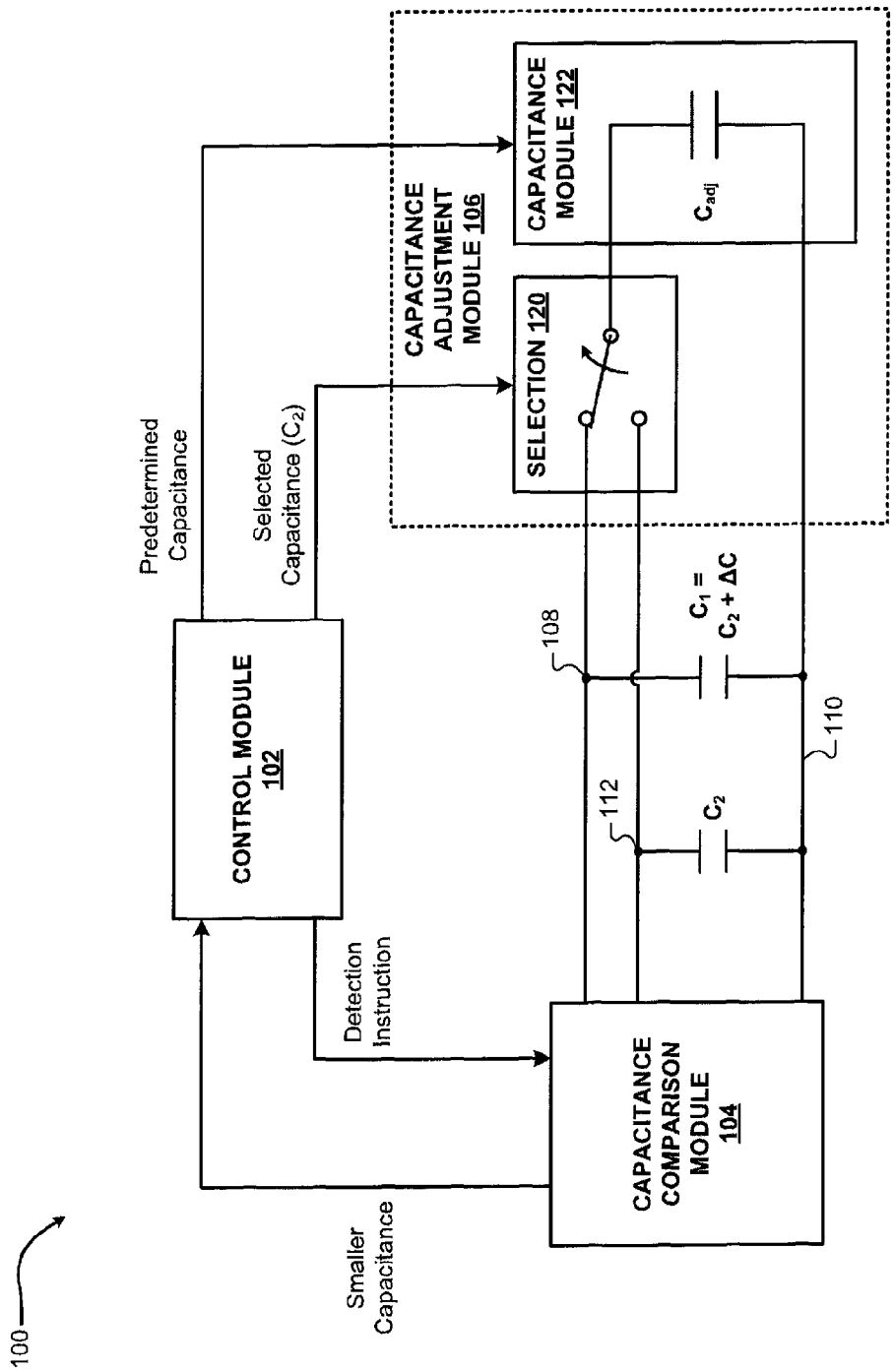
FIG. 3 is a functional block diagram of the example capacitance approximation system that illustrates a detailed view of an example capacitance adjustment module.

FIG. 3 shows a detailed view of an example capacitance adjustment module 106. Capacitance adjustment module 106 includes a selection module 120 and a capacitance module 122. Selection module 120 selectively connects either $C_1$ or $C_2$ to adjustable capacitance "$C_{adj}$" of capacitance module 122. Accordingly, selection module 120 is illustrated as a switch may connect either $C_1$ or $C_2$ to $C_{adj}$.

Selection module 120 may selectively connect either $C_1$ or $C_2$ to $C_{adj}$ based on an instruction (e.g., a binary value) received from control module 102 indicating which capacitance is selected for adjustment. In the example of FIG. 3, selection module 120 selectively connects $C_2$ to $C_{adj}$ in response to the instruction from control module 102 indicating that $C_2$ is the selected capacitance. Although selection module 120 is illustrated and described as connecting $C_2$ to $C_{adj}$ since $C_2$ is the smaller of $C_1$ and $C_2$, selection module 120 may also connect $C_1$ to $C_{adj}$ in examples where $C_1$ is smaller than $C_2$, i.e., in examples where $C_1$ is the selected capacitance.

$C_{adj}$ may represent an adjustable capacitance that may be placed in parallel with either $C_1$ or $C_2$. In some examples, $C_{adj}$ may be implemented using an array of capacitors having various predetermined values, described hereinafter with reference to FIGS. 7-8. Accordingly, in some examples, capacitance module 122 may selectively add capacitors from the array of capacitors in parallel with the selected capacitance in order to implement the adjustable capacitance $C_{adj}$. Although capacitance module 122 is described herein as including an array of capacitors that implement $C_{adj}$, it is contemplated that the adjustable capacitance $C_{adj}$ of capacitance module 122 may be implemented using other techniques.

Capacitance module 122 may set $C_{adj}$ to the amount of capacitance indicated by control module 102 (e.g., the predetermined capacitance). In examples where $C_{adj}$ is realized by an array of predetermined capacitors, control module 102 may instruct capacitance module 122 using a binary value that indicates which capacitors of the array to connect/disconnect in order to achieve the amount of capacitance (e.g., the predetermined capacitance).

Figure 4:
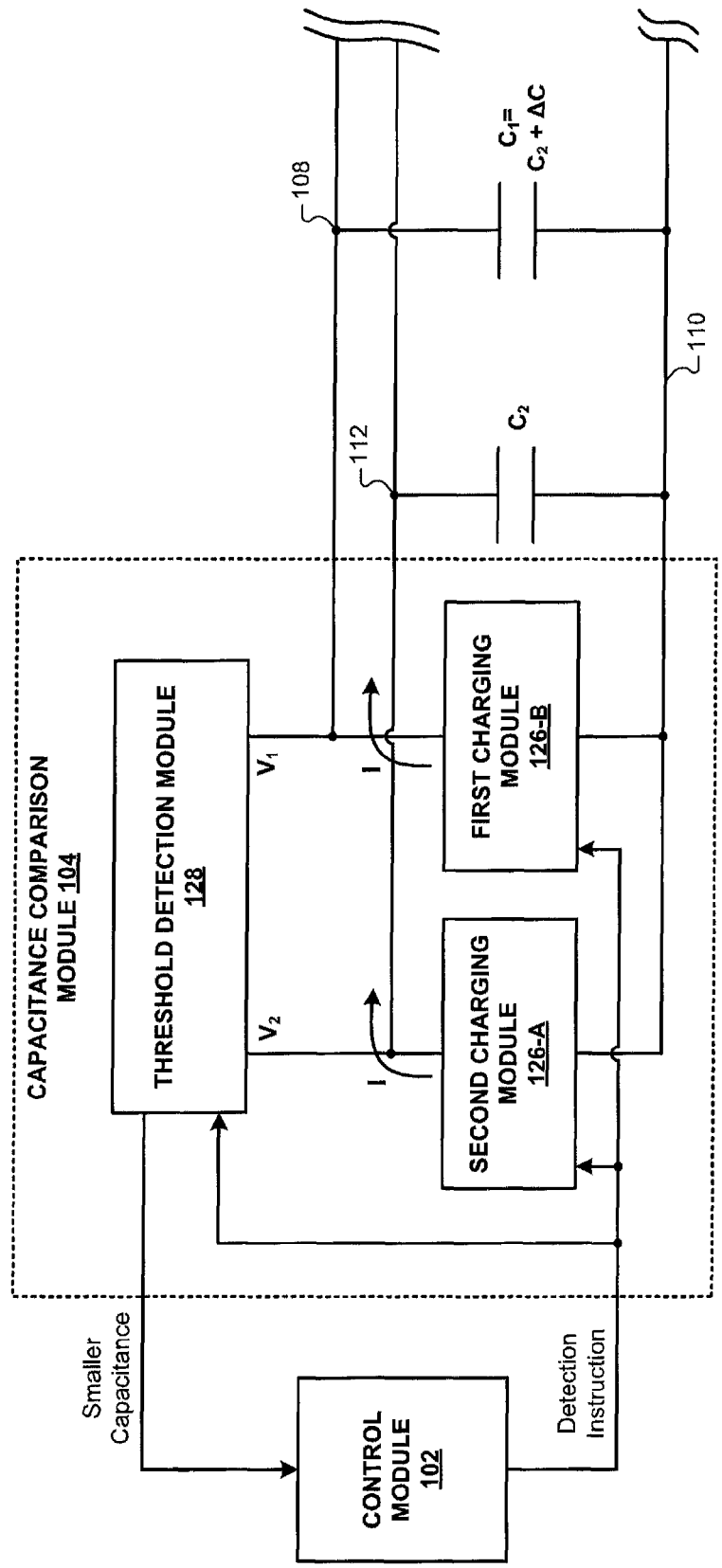
FIG. 4 is functional block diagram of an example capacitance comparison module of the capacitance approximation system of FIG. 1.

FIG. 4 shows a detailed view of an example capacitance comparison module 104. Capacitance comparison module 104 includes a first charging module 126-A, a second charging module 126-B, and a threshold detection module 128. First and second charging modules 126-A, 126-B charge capacitances $C_1$ and $C_2$, respectively. In some examples, $C_{adj}$ may be connected to either $C_1$ or $C_2$, which may result in an adjusted value of either $C_1$ or respectively, which may in turn result in an adjusted charging time of $C_1$ or $C_2$.

Threshold detection module 128 monitors voltages across $C_1$ (i.e., $V_1$) and $C_2$ (i.e., $V_2$) while first and second charging modules 126-A, 126-B are charging $C_1$ and $C_2$. Threshold detection module 128 determines which of $C_1$ and $C_2$ is smaller based on which of the monitored voltages $V_1$ and $V_2$ crosses a threshold voltage first. Additionally, threshold detection module 128 may also determine which of $C_1$ and $C_2$ is larger based on which of $C_1$ and $C_2$ does not cross the threshold voltage first.

First and second charging modules 126-A, 126-B may include current sources (e.g., constant current sources). The current sources of each of first and second charging modules 126-A, 126-B may provide equal charging currents, labeled as "I" in FIG. 4. The equal charging currents may be implemented using current mirror circuits, for example.

Charging modules 126-A, 126-B may each provide the charging currents "I" to respective capacitances $C_1$ and $C_2$ starting at the same time in response to the detection instruction from control module 102. Assuming that $C_1$ and $C_2$ are discharged prior to receiving the detection instruction from control module 102, and assuming that the first and second charging modules 126-A, 126-B deliver equal currents, starting at approximately the same time in response to the detection instruction, the voltage across the smaller of $C_1$ and $C_2$ will increase at a higher rate. Accordingly, the greater of voltages $V_1$ and $V_2$ may be the voltage across the smaller of $C_1$ and $C_2$. For example, if voltage $V_1$ increases at a higher rate than voltage $V_2$, $C_1$ may be smaller than $C_2$, and vice versa.

Threshold detection module 128 monitors voltages $V_1$ and $V_2$ while first and second charging modules 126-A, 126-B deliver current "I" to $C_1$ and $C_2$. Threshold detection module 128 monitors $V_1$ and $V_2$ to determine which of $V_1$ and $V_2$ cross the threshold voltage first. Since the smaller of $C_1$ and $C_2$ may develop voltage at a higher rate, the first of $V_1$ and $V_2$ to reach the threshold voltage corresponds to the smaller of $C_1$ and $C_2$. In other words, threshold detection module 128 detects which of $C_1$ and $C_2$ is smaller based on which of $V_1$ and $V_2$ increase beyond the threshold voltage first, after receipt of the detection instruction from control module 102.

In some implementations, threshold detection module 128 may include field effect transistor (FET) switches (e.g., metal-oxide-semiconductor FETs (MOSFETs)), the gates of which are connected to $V_1$ and $V_2$. In these implementations, threshold voltages of FET switches connected to $V_1$ and $V_2$ may serve as the predetermined threshold voltage, and current through the FET switches may serve as the indication of which of $C_1$ and $C_2$ is charged to the threshold voltage. In other words, voltages across $C_1$ and $C_2$ may be connected to gates of FET transistors and current may flow through the FET transistors, signaling, to control module 102 when the threshold voltage has been reached. In other implementations, threshold detection module 128 may include comparators that compare voltages $V_1$ and $V_2$ to the threshold voltage (e.g., a predetermined reference voltage). Accordingly, in some examples, comparators included in threshold detection module 128 may indicate when $V_1$ and $V_2$ reach the threshold voltage.

After threshold detection module 128 determines which of $C_1$ and $C_2$ is smaller, first and second charging modules 126-A, 126-B may discharge $C_1$ and $C_2$, e.g., by connecting a load in parallel with $C_1$ and $C_2$. Subsequently, first and second charging modules 126-A, 126-B may wait for the detection instruction from control module 102 before charging $C_1$ and $C_2$ again.

Although capacitance comparison module 104 is illustrated as charging $C_1$ and $C_2$, in examples where $C_{adj}$ is connected in parallel with one of $C_1$ or $C_2$, capacitance comparison module may charge $C_{adj}$ along with $C_1$ and $C_2$. Connection of $C_{adj}$ in parallel with a capacitance (e.g., $C_1$ or $C_2$) may increase the charging time of the capacitance and in turn decrease a rate at which voltage develops across the capacitance. In this manner, during the iterative approximation method, threshold detection module 128 may determine whether $C_{adj}$ added in parallel with the selected capacitance is greater than the unselected capacitance.

Figure 5:
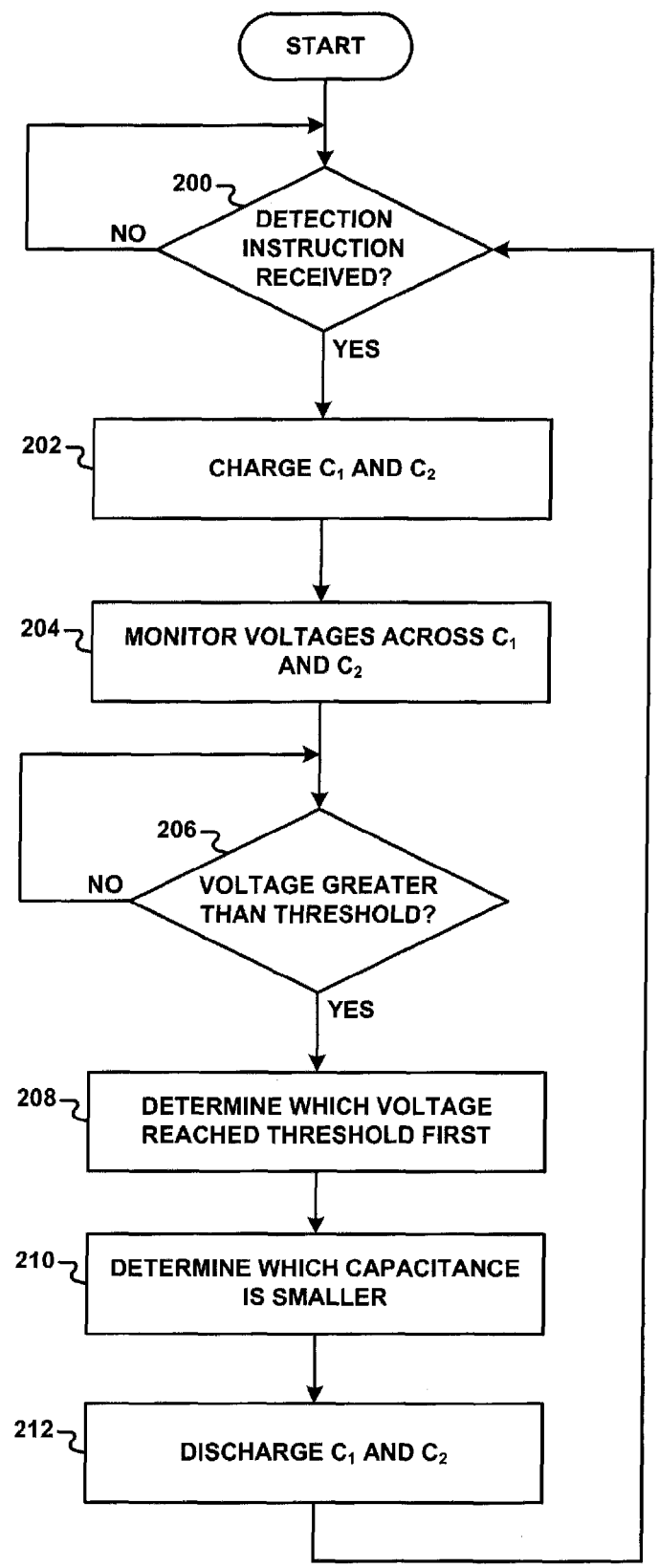
FIG. 5 illustrates an example method for determining the smaller of $C_1$ and $C_2$ of the capacitance approximation system.

FIG. 5 illustrates a method for determining which of $C_1$ and $C_2$ is smaller. At the start of the method, it is assumed that $C_1$ and $C_2$ have been discharged, e.g., so that $V_1$ and $V_2$ are approximately 0V. First, charging modules 126-A, 126-B wait for a detection instruction from control module 102 (200). If charging modules 126-A, 126-B receive the detection instruction, charging modules 126-A, 126-B start charging $C_1$ and $C_2$ (202). For example, charging modules 126-A, 126-B may connect current sources to $C_1$ and $C_2$ that provide constant current to $C_1$ and $C_2$ in order to charge $C_1$ and $C_2$.

Threshold detection module 128 monitors voltages $V_1$ and $V_2$ across $C_1$ and $C_2$, respectively, while charging modules 126-A, 126-B are charging $C_1$ and $C_2$ (204). Threshold detection module 128 determines whether $V_1$ or $V_2$ has reached the threshold voltage (206). When one of $V_1$ and $V_2$ reach the threshold voltage, threshold detection module 128 determines which of $V_1$ and $V_2$ reached the threshold voltage first (208). Threshold detection module 128 then indicates to control module 102 which of $V_1$ and $V_2$ reached the threshold voltage first (i.e., which of $C_1$ and $C_2$ is smaller) (210). For example, if $V_1$ reaches the threshold voltage first, threshold detection module 128 indicates that $C_1$ is the smaller capacitance of $C_1$ and $C_2$. Alternatively, if $V_2$ reaches the threshold voltage first, threshold detection module 128 indicates that $C_2$ is the smaller capacitance of $C_1$ and $C_2$. Charging modules 126-A, 126-B then discharge $C_1$ and $C_2$ so that $V_1$ and $V_2$ may return to zero (212). For example, charging modules 126-A, 126-B may connect loads in parallel with $C_1$ and $C_2$ to discharge $C_1$ and $C_2$.

Figure 6:
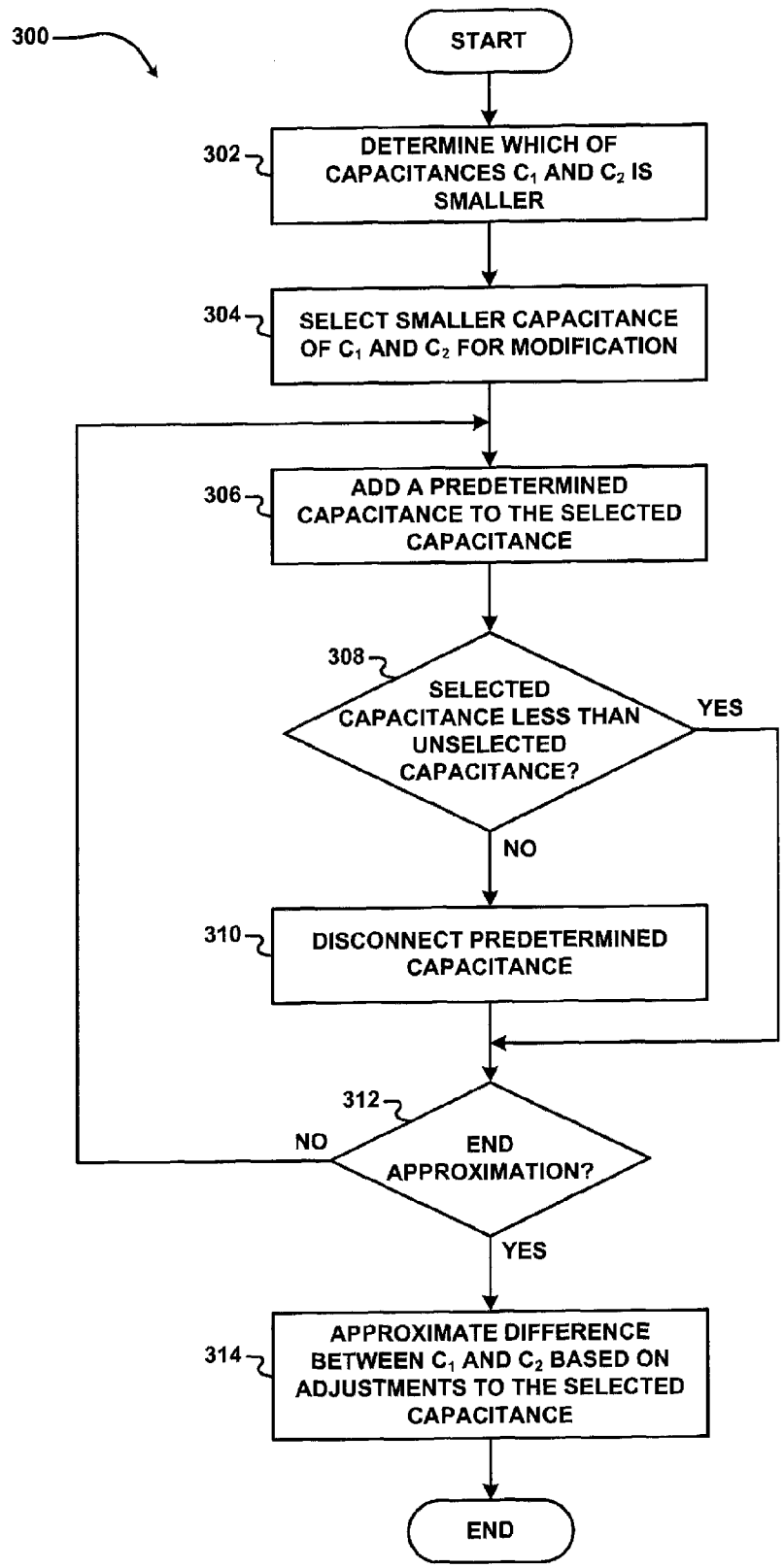
FIG. 6 illustrates an example iterative approximation method.

Referring now to FIG. 6, an example iterative approximation method 300 is shown. Control module 102 may determine $\Delta C_{approx}$ according to the iterative approximation method 300. The iterative approximation method 300 may include three phases. During the first phase, blocks (302) and (304), capacitance approximation system 100 determines which of $C_1$ and $C_2$ is smaller. In other words, during the first phase, capacitance approximation system 100 selects one of $C_1$ and $C_2$ for modification in subsequent phases.

During the second phase, blocks (306) to (312), capacitance approximation system 100 iteratively adds (e.g., in parallel), to the selected capacitance, capacitances having different predetermined values. During each iteration of blocks (306) to (312), after a predetermined capacitance is added to the selected capacitance, capacitance approximation system 100 determines whether the selected capacitance in combination with the predetermined capacitance is greater than the unselected capacitance. Subsequent to the determination, capacitance approximation system 100 removes the predetermined capacitance if the combination of the selected capacitance and the predetermined capacitance is greater than the unselected capacitance. In subsequent iterations, capacitance approximation system 100 adds capacitances having other predetermined values to the selected capacitance and determines whether each of the predetermined values in combination with the selected capacitance is greater than the unselected capacitance.

During the third phase, block (314), after a plurality of iterations of blocks (306) to (312), control module 102 approximates the difference between the selected and unselected capacitances based on which capacitances are connected to the selected capacitance. In other words, control module 102 determines $\Delta C_{approx}$ based on which predetermined capacitances, when combined with the selected capacitance, did not result in a combination of capacitances that were greater than the unselected capacitance.

The example iterative approximation method 300 is now discussed with reference to FIG. 6 under the assumption that $C_2$ is less than $C_1$, according to FIGS. 2-5. Initially, control module 102 instructs capacitance comparison module 104 to determine which of $C_1$ and $C_2$ is smaller (302). Capacitance comparison module 104 determines which of $C_1$ and $C_2$ is smaller (i.e., $C_2$) in response to the instruction from control module 102 (304). Capacitance comparison module 104 then indicates, to control module 102, which of $C_1$ and $C_2$ is smaller (i.e., indicates $C_2$). Control module 102 selects the smaller of $C_1$ and $C_2$ as the capacitance to adjust during the remaining steps of the iterative approximation method (i.e., blocks (306) to (314)). In other words, $C_2$ is the selected capacitance for the remainder of the iterative approximation method 300 and $C_1$ is the unselected capacitance for the remainder of the iterative approximation method 300.

After control module 102 selects a capacitance to modify (i.e., $C_2$), control module 102 instructs capacitance adjustment module 106 to add a predetermined capacitance to the selected capacitance. In other words, control module 102 instructs capacitance adjustment module 106 to increase the selected capacitance by a predetermined capacitance. In response to the instruction, capacitance adjustment module 106 adds the predetermined capacitance (i.e., $C_{adj}$) in parallel with the selected capacitance (i.e., $C_2$) (306). Accordingly, after block (306), the selected capacitance may be equal to the sum of the selected capacitance prior to block (306) and the predetermined capacitance added in block (306).

Control module 102 then instructs capacitance comparison module 104 to determine whether the selected capacitance (i.e., $C_2+C_{adj}$) is larger or smaller than the unselected capacitance. Capacitance comparison module 104 then determines which of the capacitances is smaller. If capacitance comparison module 104 determines that the selected capacitance (i.e., $C_2+C_{adj}$) is not less than the unselected capacitance ($C_1$), control module 102 instructs capacitance adjustment module 106 to disconnect the predetermined capacitance from the selected capacitance (310). If capacitance comparison module 104 determines that the selected capacitance (i.e., $C_2+C_{adj}$) is smaller than the unselected capacitance ($C_1$), control module 102 does not instruct capacitance adjustment module 106 to disconnect the predetermined capacitance from the selected capacitance. Accordingly, the predetermined capacitance may remain connected to the selected capacitance during further iterations in which other capacitances having other predetermined values may be added in parallel with the selected capacitance.

Control module 102 then determines whether to end the iterative approximation method (312). For example, control module 102 may end the iterative approximation method after a predetermined number of iterations have been performed.

If control module 102 decides not to end the iterative approximation method, for example, when the predetermined number of iterations has not been performed, control module 102 initiates another iteration of blocks (306) to (312). In other words, capacitance approximation system 100 performs blocks (306) to (312) of the method 300 again. If the predetermined capacitance was not removed during the prior iteration at block (310), the predetermined capacitance may remain connected during the second iteration.

During the second iteration, control module 102 instructs capacitance adjustment module 106 to add another predetermined capacitance in parallel with the selected capacitance. The predetermined capacitance added in the second iteration may be referred to as a "second predetermined capacitance."

In some implementations, the second predetermined capacitance added in the second iteration may have the same value as the predetermined capacitance added during the first iteration. In other implementations, as explained hereinafter with reference to FIGS. 7-8, the second predetermined capacitance added in the second iteration may have a different value than the predetermined capacitance added during the first iteration.

Capacitance adjustment module 106 adds the second predetermined capacitance in parallel with the selected capacitance in response to the instruction (306). In examples where the predetermined capacitance from the first iteration was not disconnected from the selected capacitance (i.e., $C_2$) during the first iteration, the selected capacitance at block (308) may be the sum of the selected capacitance from the first iteration, the predetermined capacitance added during the first iteration, and the second predetermined capacitance.

Capacitance comparison module 104, in response to an instruction from control module 102, then determines whether the increase in the selected capacitance causes the selected capacitance to be greater than the unselected capacitance (308). If the selected capacitance in combination with the second predetermined capacitance is greater than the unselected capacitance, capacitance adjustment module 106 disconnects the second predetermined capacitance (310). If the selected capacitance in combination with the second predetermined capacitance is less than the unselected capacitance, capacitance adjustment module 106 does not disconnect the second predetermined capacitance.

Control module 102 then determines whether to end the iterative approximation method (312). If control module 102 does not end the approximation method, the method continues at block (306) for a third iteration of blocks (306) to (312). If control module 102 decides to end the iterative approximation method, for example, if a predetermined number of iterations has been performed, then control module 102 approximates the difference between $C_1$ and $C_2$ (i.e., determines $\Delta C_{approx}$) (314). Control module 102 determines $\Delta C_{approx}$ based on the total of the predetermined capacitances that are still connected to the selected capacitance (i.e., $C_2$). For example, control module 102 determines that $\Delta C_{approx}$ is equal to the sum of the predetermined capacitances which are connected to the selected capacitance.

In examples in which the predetermined capacitance from the first iteration and the second predetermined capacitance from the second iteration are still connected after the end of the approximation, control module 102 may determine that $\Delta C_{approx}$ is equal to the sum of the predetermined capacitance from the first iteration and the second predetermined capacitance. In examples in which the predetermined capacitance from only the first iteration is connected after the end of the approximation, control module 102 may determine that $\Delta C_{approx}$ is equal to the predetermined capacitance from the first iteration. In examples in which only the second predetermined capacitance from the second iteration is connected, control module 102 may determine that $\Delta C_{approx}$ is equal to the second predetermined capacitance. In examples in which neither the predetermined capacitance from the first iteration nor the second predetermined capacitance are connected, control module 102 determines that $\Delta C_{approx}$ is less than the smaller of the predetermined capacitance from the first iteration and the second predetermined capacitance.

Figure 7:
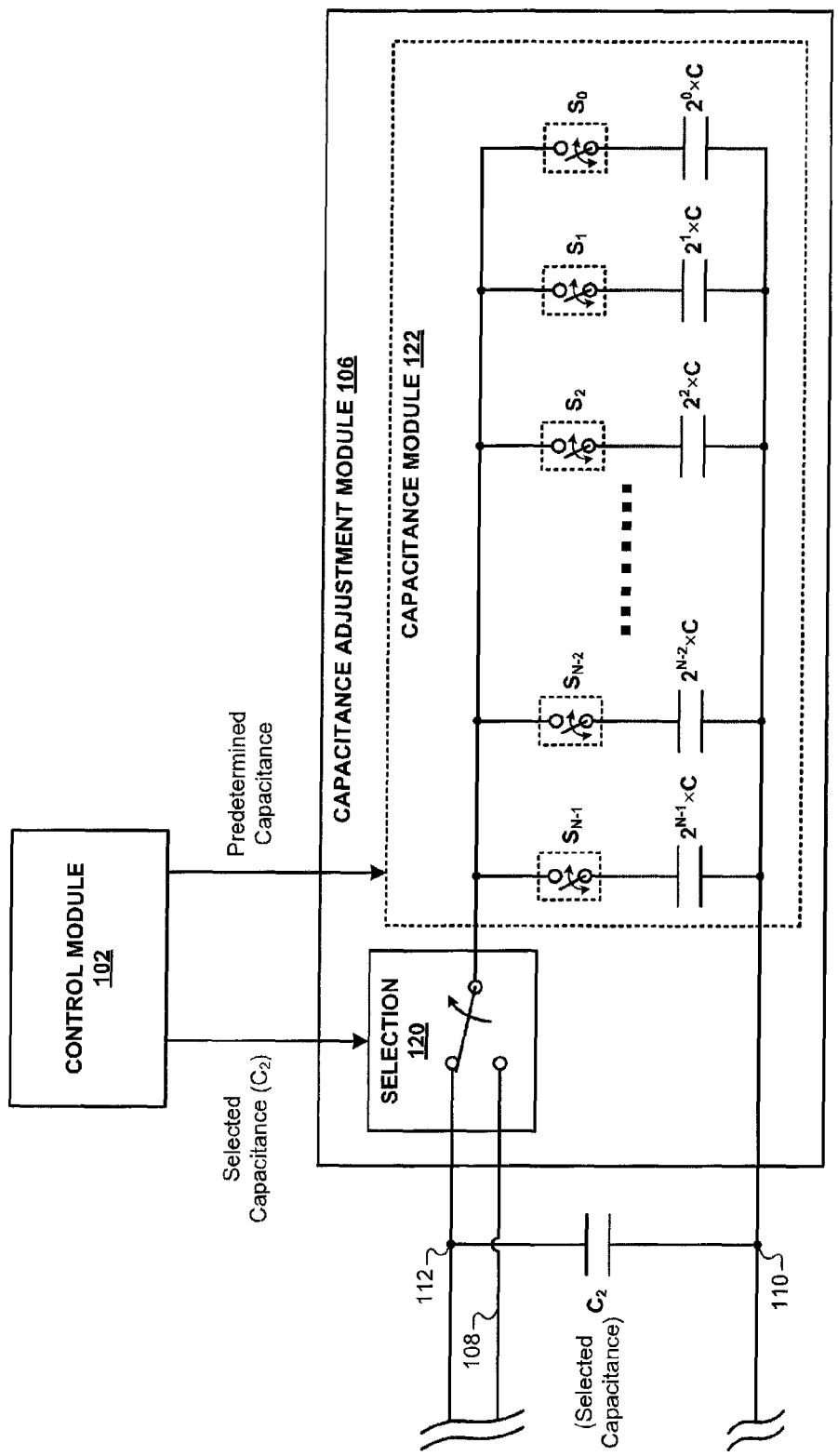
FIG. 7 is a functional block diagram that illustrates a detailed view of an example capacitance adjustment module of the capacitance approximation system of FIG. 1.

Referring now to FIG. 7, a detailed view of an example capacitance adjustment module 106 is shown to further illustrate an example implementation of capacitance approximation system 100. Capacitance module 122 includes N capacitors. Capacitance module 122 also includes N switches that may selectively connect or disconnect each of the N capacitors to the selected capacitance $C_2$. Each of the N capacitors includes a label that indicates their respective values. The capacitor on the far right of capacitance module 122 has a capacitance C (e.g., in units of Farads) and may be connected to the selected capacitance via switch $S_0$. The capacitor to the left of C has a capacitance of 2C (i.e., twice the capacitance of C) and may be connected to the selected capacitance via switch $S_1$. The capacitor on the far left may be the largest capacitance, having a value of $C \times 2^{N-1}$, and may be connected to the selected capacitance via switch $S_{N-1}$.

Control module 102 may instruct capacitance module 122 to open/close any, or all, of switches $S_0$ to $S_{N-1}$. Capacitance module 122, in response to an instruction from control module 102, may open/close any of switches $S_0$ to $S_{N-1}$, and therefore may selectively connect/disconnect any of capacitors C to $C \times 2^{N-1}$ to/from the selected capacitance. For example, capacitance module 122 may open all of switches $S_0$ to $S_{N-1}$ to disconnect all capacitors C to $C \times 2^{N-1}$ from the selected capacitance. As another example, capacitance module 122 may close all switches $S_0$ to $S_{N-1}$ to connect all capacitances to the selected capacitance. During the iterative approximation method, capacitance module 122 may selectively connect any of the capacitors C to $C \times 2^{N-1}$ in response to instructions from control module 102.

Capacitance adjustment module 106 may selectively couple any combination of capacitances C to $C \times 2^{N-1}$ to achieve any combination of discrete capacitor values. Accordingly, capacitance module 122 may selectively produce a predetermined capacitance value that may be connected in parallel to the selected capacitance and which may corresponding to any combination of capacitors C to $C \times 2^{N-1}$. A minimum achievable capacitance value may be C, while a maximum achievable capacitance value may be the sum of all capacitors from C to $C \times 2^{N-1}$.

Capacitance module 122 may selectively couple any combination of capacitors to the selected capacitance in response to an instruction from control module 102, illustrated as "Predetermined Capacitance" in FIG. 7. In the example capacitance module 122 of FIG. 7, since the capacitor array includes N capacitors, control module 102 may instruct capacitance module to connect/disconnect the N capacitors using an N bit binary value. Each of the N bits of the binary value may correspond to one of the N switches of capacitance module 122. Capacitance module 122 may close a switch in response to a bit value of 1. Capacitance module 122 may open a switch in response to a bit value of 0. In some examples, switches $S_0$ to $S_{N-1}$ may be transistor switches, or transmission gates, that selectively connect capacitors C to $C \times 2^{N-1}$ to the selected capacitance based on the binary value received from control module 102. In other words, each of the N bit binary values generated by control module 102 may represent a signal that controls a switch connecting one of the N capacitors to the selected capacitance.

Since the N capacitors illustrated in FIG. 7 are binary-weighted, the N bit value set by control module 102 may be readily translated in a digital implementation, e.g., by control module 102, into an amount of capacitance that is added to the selected capacitance. For example, if control module 102 stores the value C, when control module 102 instructs capacitance module 122 using the value 0001, control module 102 may determine that a value of C will be added in parallel to the selected capacitance in response to the instruction. As a further example, if control module 102 stores the value $C_1$, control module 102 may determine that a value of 3C will be added to the selected capacitance in response to the instruction 0011. Accordingly, control module 102 may determine, based on the value C, what amount of capacitance will be added to the selected capacitance in response to any binary instruction that the control module 102 may generate. Furthermore, since the N capacitors are binary-weighted, and represented by a binary value, the value of the capacitance added to the selected capacitance may be directly determined by a digital system and stored as a binary representation in a digital system, without any conversion prior to storage. The direct determination of capacitance by the digital system may eliminate the need for amplifiers and associated A/D converters typically used in capacitance measurement circuits since capacitance approximation system 100 is itself an A/D converter that determines a digital value.

Figure 8:
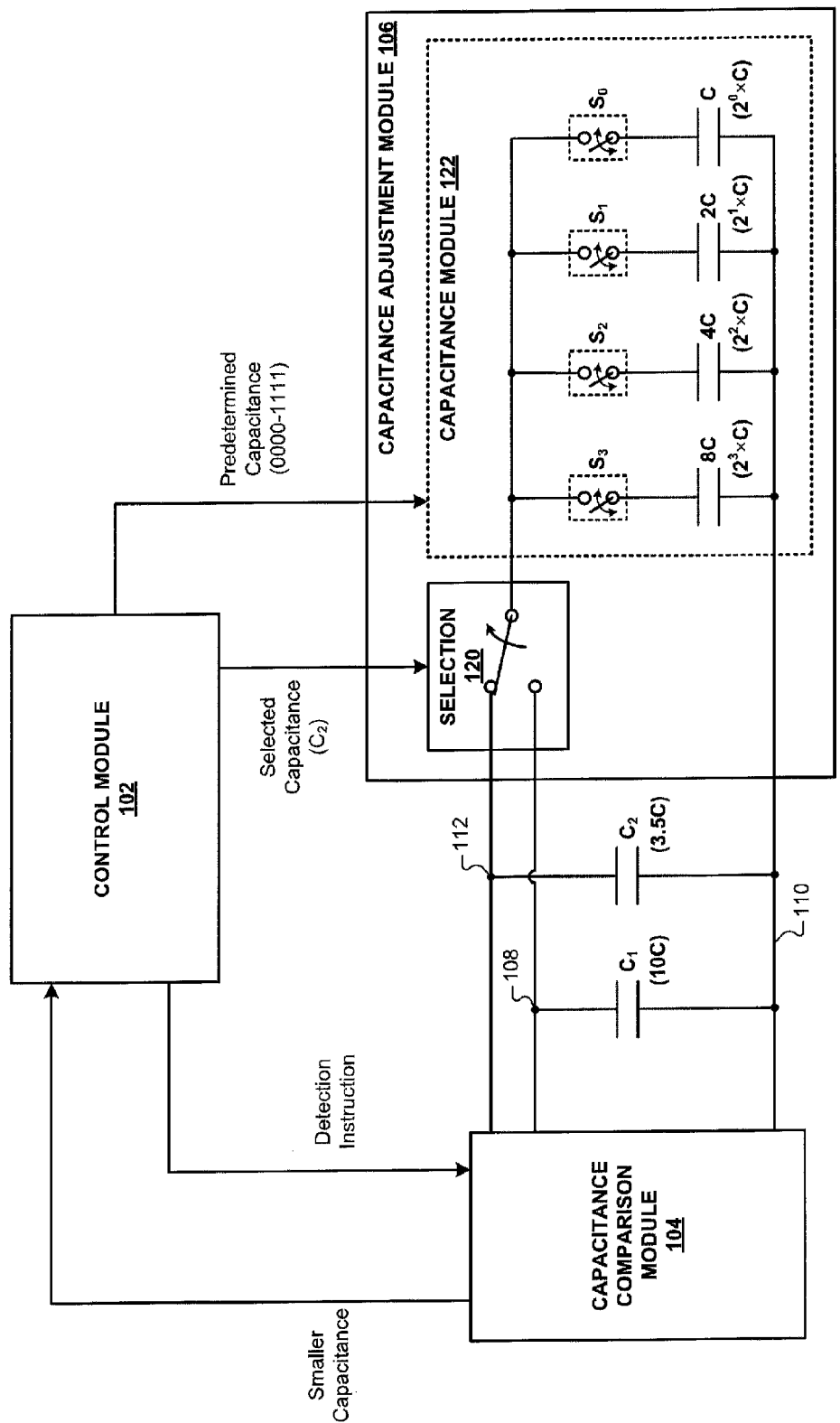
FIG. 8 is a functional block diagram that illustrates a detailed view of another example capacitance adjustment module of the capacitance approximation system of FIG. 1.

A numerical example of capacitance approximation system 100 implementing the iterative approximation method is now described with reference to FIGS. 8-9. Example capacitance module 122, as shown in FIG. 8, includes four capacitors (i.e., N=4) which are binary weighted (e.g., C, 2C, 4C, and 8C). Control module 102 may set a 4-bit binary value (e.g., 0000-1111) that controls which of the four capacitors are connected to the selected capacitance $C_2$. For example, a binary value 1000 may indicate that the largest capacitor (i.e., 8C) should be connected to the selected capacitance. As an additional example, a binary value 1111 may indicate that all of the capacitors should be connected to the selected capacitance.

In the example of FIG. 8, $C_1$=10C and $C_2$=3.5C. Operation of the capacitance approximation system 100 as illustrated in FIG. 8 is now described using the capacitance values of $C_1$, $C_2$, and capacitance module 122.

FIG. 9 is a table that illustrates, for each iteration of the method, binary values set by control module 102, the combined capacitance of the selected capacitance and capacitance from capacitance module 122, comparison results of the capacitances $C_1$ and $C_2$ by capacitance comparison module 104, and a decision made by control module 102 in response to the comparison.

During the first phase of the iterative approximation method, control module 102 instructs selection module 120 not to connect any capacitors of capacitance module 122 to either $C_1$ or $C_2$. In other words, control module 102 initially instructs selection module 120 not to connect capacitance module 122 to either $C_1$ or $C_2$. Control module 102 then instructs capacitance comparison module 104 to determine which of $C_1$ and $C_2$ is smaller. Capacitance comparison module 104 then determines which of $C_1$ and $C_2$ is smaller. Since $C_2$ (3.5C) is smaller than $C_1$ (10C), capacitance comparison module 102 may charge $C_2$ to the threshold voltage at a faster rate, and accordingly, capacitance comparison module 104 may determine that $C_2$ is smaller than $C_1$. Control module 102 may then instruct selection module 120 to connect $C_2$ to capacitance module 122. Initially, upon connection of $C_2$ to capacitance module 122 via selection module 120, capacitance module 122 may not have any capacitors connected to $C_2$ via switches $S_0$-$S_3$.

At the start of the second phase of the iterative approximation method, during the first iteration, capacitance module 122 may connect the largest capacitor (i.e., 8C) to $C_2$ in response to an instruction (e.g., 1000) from control module 102. Control module 102 then instructs capacitance comparison module 104 to determine which is larger, $C_1$, or the combination of $C_2$ with 8C. During the first iteration, capacitance comparison module 104 determines that the combination of $C_2$ and 8C (i.e., 11.5C) is greater than unselected capacitance $C_1$. Control module 102, based on results of the comparison, instructs capacitance module 122 to disconnect 8C from $C_2$. Capacitance module 122, in response to the instruction (e.g., 0000) from control module 102, then disconnects 8C from $C_2$ via switch $S_3$.

During the second iteration, capacitance module 122 may connect the second largest capacitor (i.e., 4C) to $C_2$ in response to an instruction (e.g., 0100) from control module 102. Although control module 102 is described above as setting instruction 0000 to disconnect 8C from $C_2$, then setting instruction 0100 to connect 4C to $C_2$, control module 102 may perform both tasks by transitioning the instruction in a single step from 1000 to 0100 since the transition would both disconnect 8C and connect 4C. During the second iteration, capacitance comparison module 104 determines that the combination of $C_2$ and 4C (i.e., 7.5C) is less than unselected capacitance $C_1$. Control module 102, therefore, does not instruct capacitance module 122 to disconnect capacitor 4C from $C_2$.

During the third iteration, capacitance module 122 may connect the third largest capacitor (i.e., 2C) to $C_2$ in response to an instruction (e.g., 0110) from control module 102. During the third iteration, capacitance comparison module 104 determines that the combination of $C_2$ and 4C and 2C (i.e., 9.5C) is less than unselected capacitance $C_1$. Control module 102, therefore, does not instruct capacitance module 122 to disconnect capacitor 2C from $C_2$.

During the fourth iteration, capacitance module 122 may connect the fourth largest capacitor (i.e., C) to $C_2$ in response to an instruction (e.g., 0111) from control module 102. During the fourth iteration, capacitance comparison module 104 determines that the combination of $C_2$ and 7C (i.e., 10.5C) is greater than unselected capacitance $C_1$. Capacitance module 122, in response to instruction from control module 102 (e.g., 0110), may then disconnect the fourth largest capacitor (i.e., C).

In the example of FIG. 8, the predetermined number of iterations stored by control module 102 may be 4, and accordingly, the fourth iteration may be the final iteration of the iterative approximation method. In other words, control module 102 may end the iterative approximation method after 4 iterations. Four iterations for the example of FIG. 8 may be sufficient for the approximation of $\Delta C$ since each of the 4 different capacitors included in the capacitance module 122 was connected during the approximation. In other implementations in which capacitance module 122 includes more or less capacitors, the predetermined number of iterations may be more or less. For example, if capacitance module 122 included 7 capacitors, the predetermined number of iterations may be 7, i.e., one iteration for connecting each of the capacitors. As an additional example, if capacitance module 122 included 3 capacitors, the predetermined number of iterations may be 3, i.e., one iteration for connecting each of the capacitors.

In the example of FIGS. 8 and 9, control module 102 may determine $\Delta C_{approx}$ based on which capacitors were connected after the predetermined number (i.e., 4) of iterations. In other words, control module 102 may determine $\Delta C_{approx}$ based on the maximum amount of capacitance that may be connected to the selected capacitance without causing the selected capacitance to be greater than the unselected capacitance. In the example of FIG. 8 and FIG. 9, control module 102 may determine that $\Delta C$ is approximately equal to 6C (i.e., $\Delta C_{approx}=6C$) since the connection of 4C and 2C may be the largest capacitance that may be connected to the selected capacitance without causing the selected capacitance ($C_2$) to be greater than the unselected capacitance ($C_1$). In other words, since a final instruction (e.g., 0110) of control module 102 instructed capacitance module 122 to connect 4C and 2C to the selected capacitance, control module 102 may determine that $\Delta C_{approx}$ is equal to 6C.

Figure 10:
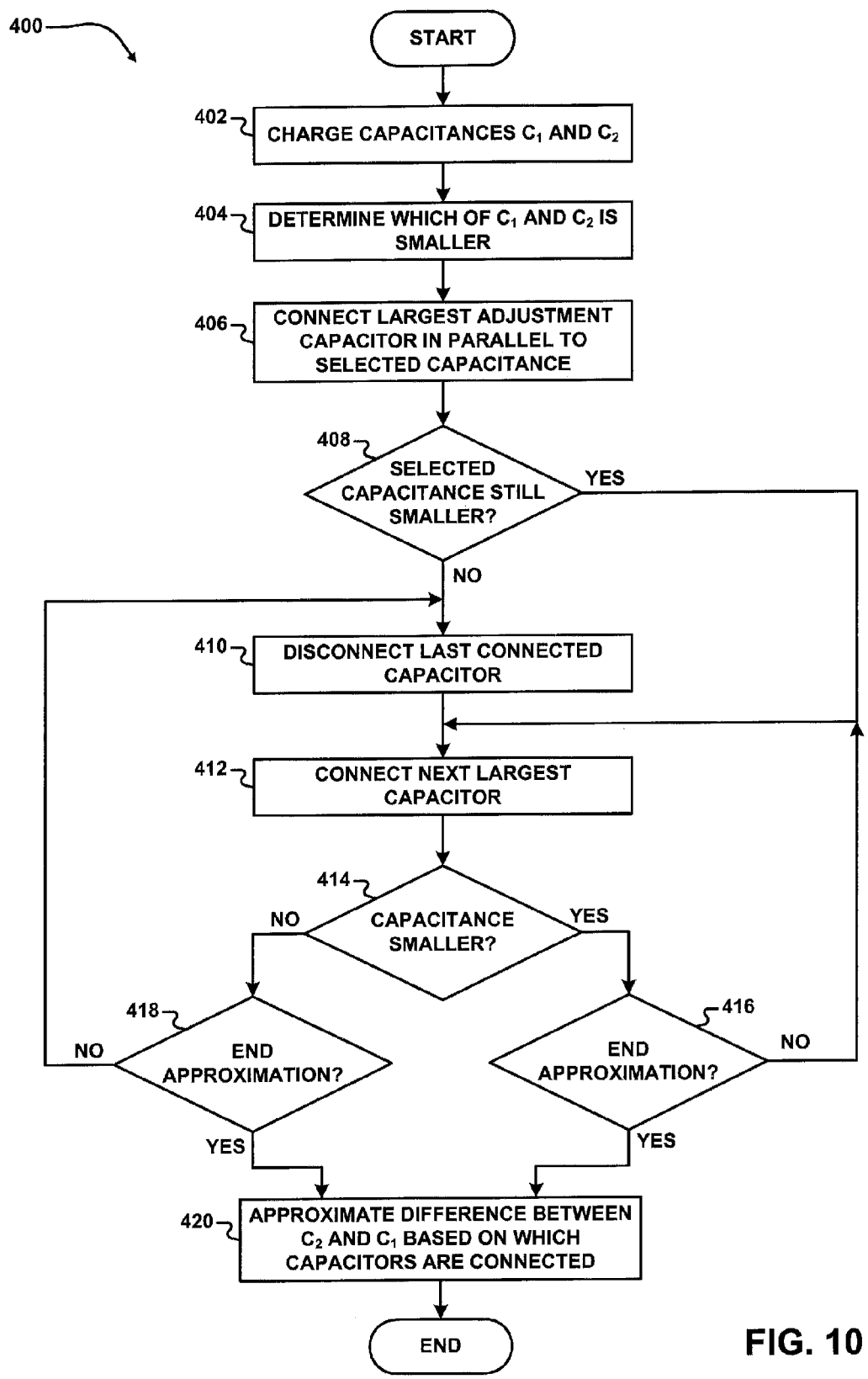
FIG. 10 illustrates an example iterative approximation method implemented using an array of capacitors having predetermined values.

Referring now to FIG. 10, an example iterative approximation method 400 implemented using an array of capacitors having predetermined values is shown. The example illustrated in FIGS. 8-9 is referenced when describing method 400 in order to illustrate one example implementation of the method 400.

Initially, control module 102 instructs capacitance comparison module 104 to determine which of $C_1$ and $C_2$ is smaller. Capacitance comparison module 104 charges $C_1$ and $C_2$ in response to the instruction (402). Capacitance comparison module 104 then determines which of $C_1$ and $C_2$ is smaller (404). The smaller of $C_1$ and $C_2$ may be referred to as the "selected capacitance." In examples where control module 102 actuates selection module 120 using a binary value (e.g., 0 or 1) that represents which of $C_1$ and $C_2$ are connected, the binary value may indicate the relative magnitude of $C_1$ and $C_2$. Accordingly, the binary value may be used as a sign bit that indicates the sign of $\Delta C_{approx}$.

Control module 102 instructs capacitance module 122 to connect the largest capacitor of capacitance module 122 in parallel with the selected capacitance. For example, in FIG. 8, control module 102 would instruct capacitance module 122 to connect capacitor 8C in parallel with $C_2$. Control module 102 then instructs capacitance comparison module 104 to determine whether the selected capacitance in parallel with the largest capacitor is still smaller than the unselected capacitance (408). For example, in FIG. 8, control module 102 would instruct capacitance comparison module 104 to determine whether $C_2$ in parallel with 8C is less than 10C. If comparison module 104 determines that the selected capacitance in parallel with the largest capacitor is larger than the unselected capacitance, capacitance module 122 disconnects the largest capacitor, in response to an instruction from control module 102 (410). Disconnection of the largest capacitance (i.e., 8C) was illustrated in the example of FIG. 8. If capacitance comparison module 104 determines that the selected capacitance in parallel with the largest capacitor is smaller, capacitance module 122 connects the next largest capacitor in parallel with the selected capacitance (412). In the example of FIG. 8, the largest capacitance (i.e., 8C) was disconnected and the next largest capacitance (i.e., 4C) was connected according to blocks (410) and (412).

Capacitance comparison module 104 then compares the relative magnitude of the selected capacitance with the unselected capacitance after connection of the next largest capacitance (414). In the example of FIG. 8, capacitance comparison module 104 compared capacitance $C_1$ to capacitance $C_2$ in parallel with 4C. If capacitance comparison module 104 determines that the selected capacitance is smaller than the unselected capacitance, control module 102 determines whether to end the iterative approximation in block (416). If capacitance comparison module 104 determines that the selected capacitance is not smaller than the unselected capacitance, control module 102 determines whether to end the iterative approximation in block (418). For example, control module 102 may determine whether to end the iterative approximation in blocks (416) or (418) based on whether a predetermined number of iterations have been performed. In the example of FIG. 8, the predetermined number of iterations may be 4, since 4 iterations may be required to connect and compare each of the 4 capacitors.

If control module 102 decides not to end the iterative approximation, the method 400 may continue in either block (412) or block (410), depending on whether the selected capacitance, as modified by the capacitor connected in parallel, was greater than or less than the unselected capacitance in block (414). In the example of FIG. 8, the method 400 would continue in block (412), where capacitor 2C would be connected in parallel with $C_2$ and 4C.

If control module 102 decides to end the iterative approximation in either block (416) or block (418), control module 102 approximates the difference between $C_2$ and $C_1$ (420). Control module 102 may determine $\Delta C_{approx}$ based on the final instruction (e.g., binary instruction) set to control capacitance module 122. In the example of FIG. 8, since a final instruction (e.g., 0110) of control module 102 instructed capacitance module 122 to connect 4C and 2C to the selected capacitance, control module 102 may determine that $\Delta C_{approx}$ is equal to 6C. Stated another way, control module 102 may approximate $\Delta C$ based on which capacitors are connected to the selected capacitance after the predetermined number of iterations.

Figure 11:
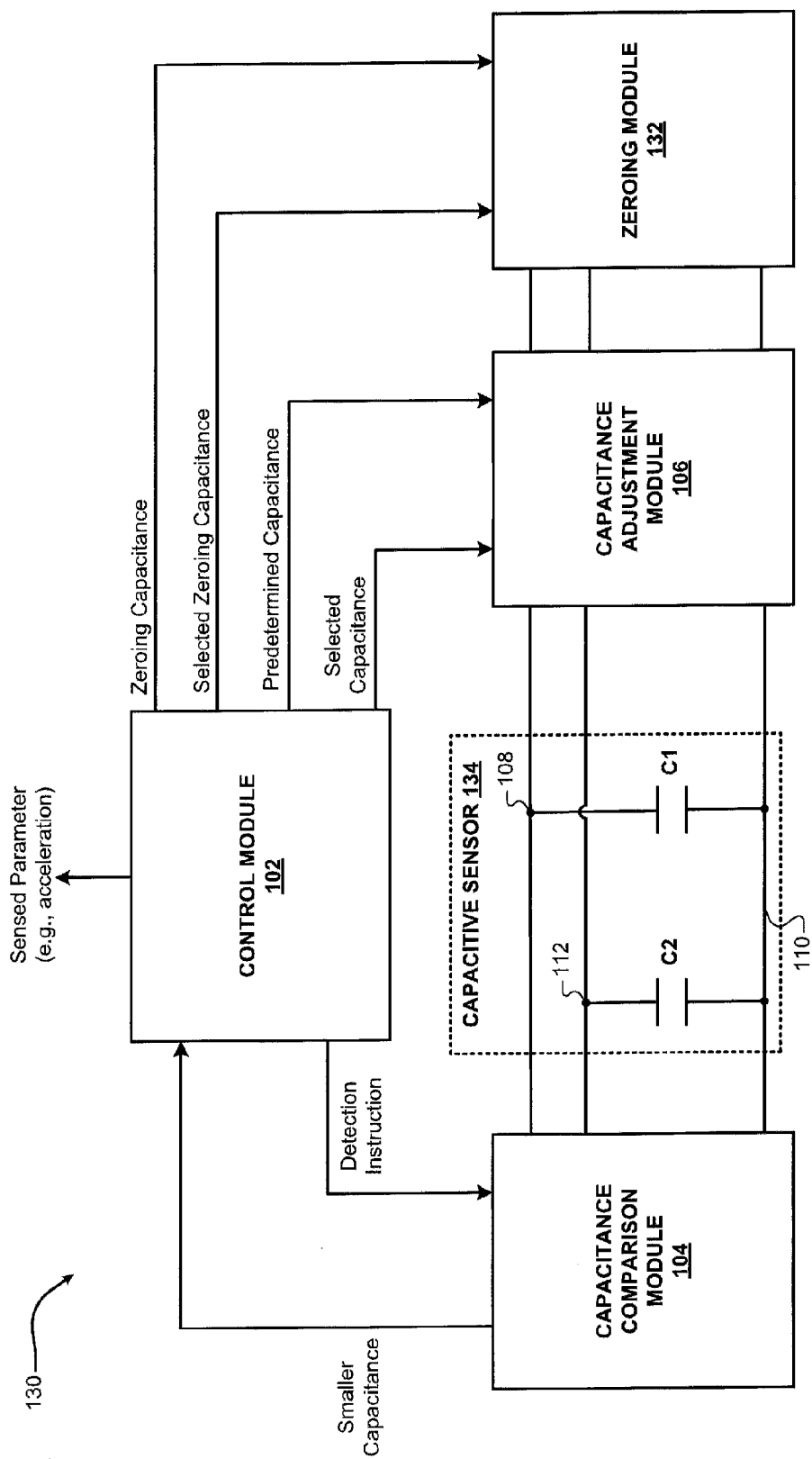
FIG. 11 is a functional block diagram of an example capacitance approximation system that includes a zeroing module.
Figure 12:
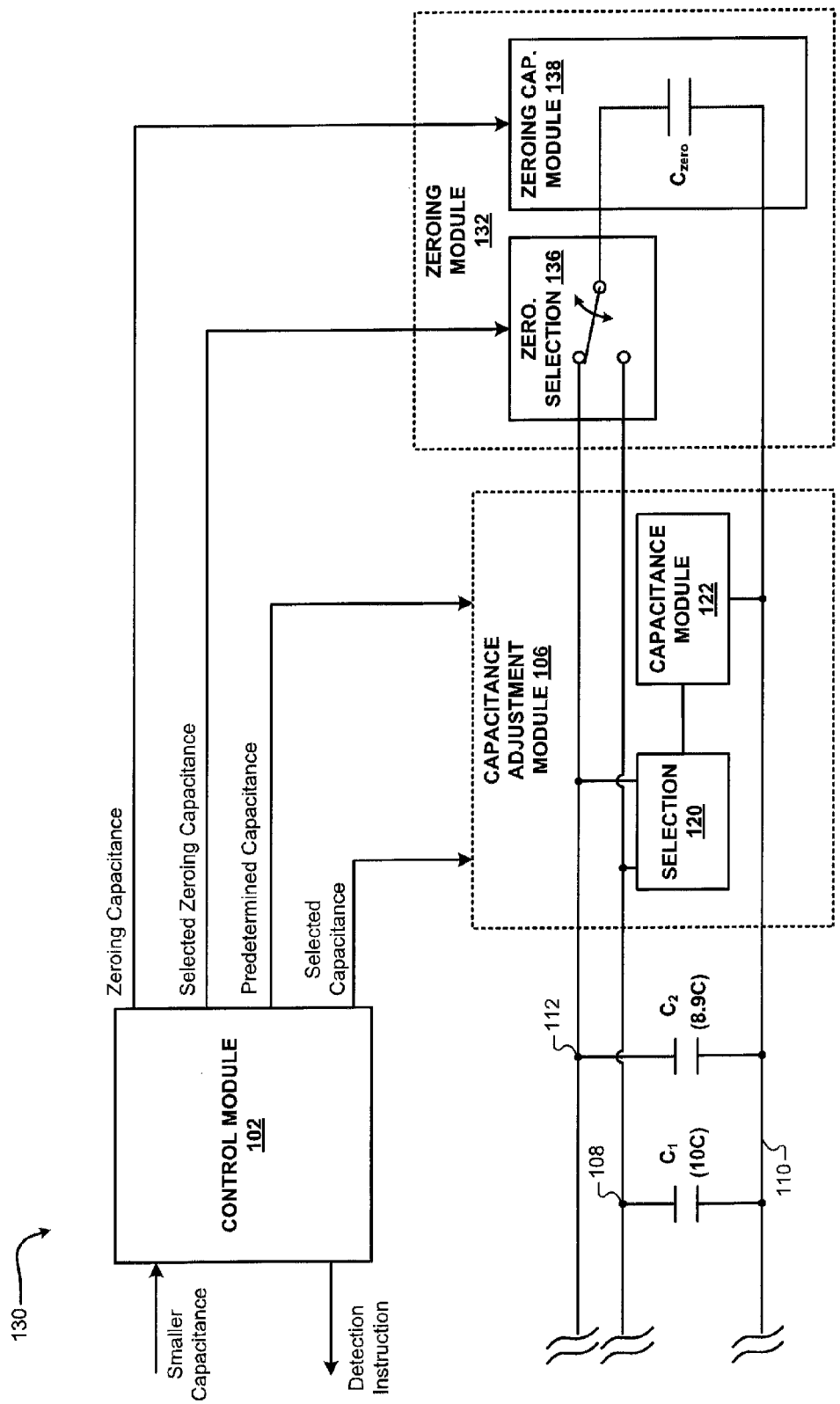
FIG. 12 illustrates a detailed view of an example zeroing module of the capacitance approximation system of FIG. 11.

FIGS. 11-12 illustrate another capacitance approximation system 130 which is similar to capacitance approximation system 100 of FIGS. 1 and 2, except that capacitance approximation system 130 of FIG. 11 includes a zeroing module 132, and $C_1$ and $C_2$ are illustrated as included in a capacitive sensor 134. Zeroing module 132 may be used in capacitance approximation system 130 to set an initial difference (e.g., due to tolerances) between $C_1$ and $C_2$ to approximately zero. For example, zeroing module 132 may include an array of capacitors, similar to capacitance adjustment module 106 that may be added in parallel with the smaller of $C_1$ and $C_2$ to set the difference between $C_1$ and $C_2$ to zero. Use of zeroing module 132 to set the difference between $C_1$ and $C_2$ to approximately zero may be referred to as a "zeroing operation."

In one example, when $C_1$ and $C_2$ are included in capacitive sensor 134, a zeroing operation may be used, e.g., to eliminate a $\Delta C$ value that is present in capacitive sensor 134 in the absence of input. For example, if the capacitive sensor 134 is an accelerometer, $\Delta C$ may indicate an amount of acceleration of the accelerometer, and accordingly, the zeroing operation may be used to eliminate a $\Delta C$ that may indicate acceleration, when in reality, the accelerometer is not subjected to acceleration. In some examples, $\Delta C$ may be on the order of 5 pF.

For purposes of illustration, it will be assumed hereinafter that capacitive sensor 134 is an accelerometer in which $\Delta C$ indicates an amount of acceleration experienced by capacitive sensor 134. Although capacitive sensor 134 is described hereinafter as an accelerometer, capacitive sensor 134 may include different types of capacitive sensors that measure parameters other than acceleration. For example, capacitive sensor 134 may include, but is not limited to, a sensor that detects temperature, humidity, pressure, position, or gases (e.g., mercury, hydrogen, carbon dioxide, carbon monoxide, etc.). Accordingly, capacitance approximation system 130 may approximate different sensed parameters depending on the type of parameter indicated by capacitive sensor 134.

Control module 102 may approximate the amount of acceleration experienced by capacitive sensor 134, i.e., may determine $\Delta C_{approx}$, by implementing the iterative approximation method. However, if there is a difference (e.g., due to manufacturing tolerances) between $C_1$ and $C_2$ when the accelerometer is at rest, $\Delta C_{approx}$ determined during the iterative approximation method may not be an accurate representation of actual acceleration of the accelerometer, but instead may indicate both acceleration and initial offset.

Capacitance approximation system 130 may perform a zeroing operation on capacitive sensor 134 in the absence of input (e.g., zero acceleration) to capacitive sensor 134 in order to zero capacitive sensor 134. In the absence of input, any difference between $C_1$ and $C_2$ may be an amount of capacitance that does not indicate acceleration. Accordingly, the zeroing operation may be performed in order to eliminate any difference between $C_1$ and $C_2$, so that at rest (i.e., zero acceleration), $\Delta C$ is approximately 0.

In general, zeroing module 132, under control of control module 102 may add capacitance to the smaller of $C_2$ and $C_1$ in a manner similar to the iterative approximation method described above. For example, control module 102 may control zeroing module 132 to add an amount of capacitance to the smaller of $C_1$ and $C_2$ without causing the initially smaller capacitance of $C_1$ and $C2$ to be greater than the initially larger of $C_1$ and $C_2$. The capacitance that may be added by zeroing module 132 without causing the initially smaller of $C_1$ and $C_2$ to be greater than the initially larger of $C_1$ and $C_2$ may be referred to as a "zeroing capacitance ($C_{zero}$)."

Referring now to FIG. 12, a detailed view of an example zeroing module 132 is shown. Zeroing module 132 includes a zeroing selection module 136 and a zeroing capacitance module 138. Control module 102 may control zeroing selection module 136 and zeroing capacitance module 138 in a similar manner to selection module 120 and capacitance module 122 during the iterative approximation method. As illustrated in FIG. 12, selection module 120 may selectively connect either $C_1$ or $C_2$ to capacitance module 122 as described above. Independent of the selection made by selection module 120, zeroing selection module 136, under control of control module 102 may selectively connect either $C_1$ or $C_2$ to zeroing capacitance module 138 to connect $C_{zero}$ in parallel with either $C_1$ or $C_2$.

Similarly to the iterative approximation method described above, capacitance approximation system 130 may perform an iterative zeroing method in order to reduce a difference between $C_1$ and $C_2$ (e.g., due to manufacturing tolerances). The iterative zeroing method may be performed when capacitive sensor 134 is not subjected to input. For example, when capacitive sensor 134 is an accelerometer, the iterative zeroing method may be performed when capacitive sensor 134 is at not subject to acceleration (e.g., at rest, or a constant velocity). Control module 102 may subsequently implement the iterative approximation method while the zeroing capacitance ($c_{zero}$) is connected in order to determine an amount of acceleration experienced by capacitive sensor 134. In this manner, implementation of the iterative approximation method subsequent to the iterative zeroing method may result in a determination of $\Delta C_{approx}$ that indicates a sensed parameter and does not indicate an initial offset between $C_1$ and $C_2$, due, for example, to a manufacturing tolerance error.

Figure 13:
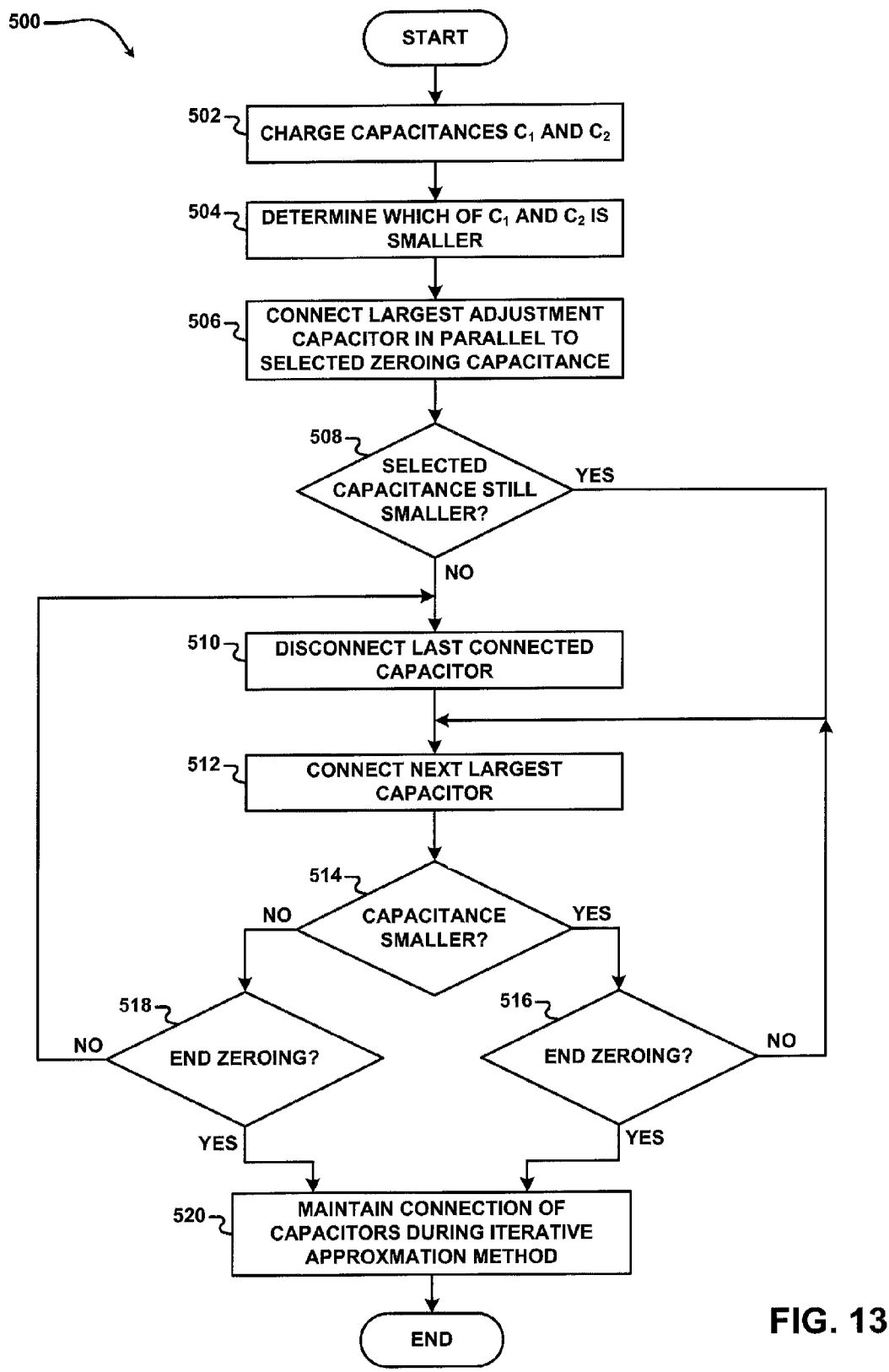
FIG. 13 is an example iterative zeroing method implemented using an array of capacitors having predetermined values.

Referring now to FIG. 13, an example iterative zeroing method 500 implemented using an array of capacitors having predetermined values is shown. To illustrate the iterative zeroing method 500, it is assumed that zeroing capacitance module 138 includes an array of capacitors having the same values as capacitance module 122 in FIG. 8 (i.e., C, 2C, 4C, and 8C). For purposes of illustration, it may be assumed that $C_1$ and $C_2$ include offsets, e.g., due to manufacturing tolerances, such that in the absence of input, $C_1$=10C and $C_2$=8.9C.

At the start of the iterative zeroing method, initially, control module 102 instructs capacitance comparison module 104 to determine which of $C_1$ and $C_2$ is smaller. Capacitance comparison module 104 charges $C_1$ and $C_2$ in response to the instruction (502). Capacitance comparison module 104 then determines which of $C_1$ and $C_2$ is smaller (504). The smaller of $C_1$ and $C_2$ may be referred to as the "selected zeroing capacitance" since capacitors may be added to it in order to "zero" the difference between $C_1$ and $C_2$. The larger of $C_1$ and $C_2$ may be referred to as the "unselected zeroing capacitance."

Control module 102 instructs zeroing module 132 to connect the largest capacitor of zeroing capacitance module 138 in parallel with the selected zeroing capacitance (506). For example, in FIG. 12, control module 102 would instruct zeroing capacitance module 122 to connect capacitor 8C in parallel with $C_2$. Control module 102 then instructs capacitance comparison module 104 to determine whether the selected zeroing capacitance in parallel with the largest capacitor is still smaller than the unselected zeroing capacitance (508). For example, in FIG. 12, control module 102 would instruct capacitance comparison module 104 to determine whether $C_2$ in parallel with 8C is less than 10C. If comparison module 104 determines that the selected zeroing capacitance in parallel with the largest capacitor is larger than the unselected zeroing capacitance, zeroing capacitance module 122 disconnects the largest capacitor, in response to an instruction from control module 102 (510). If capacitance comparison module 104 determines that the selected zeroing capacitance in parallel with the largest capacitor is smaller, zeroing capacitance module 122 connects the next largest capacitor in parallel with the selected capacitance (512). In the example of FIG. 12, the largest capacitance (i.e., 8C) would be disconnected and the next largest capacitance (i.e., 4C) would be connected according to blocks (510) and (512).

Capacitance comparison module 104 then compares the relative magnitude of the selected zeroing capacitance with the unselected zeroing capacitance after connection of the next largest capacitance (514). In the example of FIG. 12, capacitance comparison module 104 would compare capacitance $C_1$ to capacitance $C_2$ in parallel with 4C. If capacitance comparison module 104 determines that the selected zeroing capacitance is smaller than the unselected zeroing capacitance, control module 102 determines whether to end the iterative zeroing in block (516). If capacitance comparison module 104 determines that the selected zeroing capacitance is not smaller than the unselected zeroing capacitance, control module 102 determines whether to end the iterative zeroing in block (518). For example, control module 102 may determine whether to end the iterative zeroing in blocks (516) or (518) based on whether a predetermined number of iterations have been performed. In the example of FIG. 12, the predetermined number of iterations may be 4, since 4 iterations may be required to connect and compare each of the 4 capacitors of zeroing capacitance module 138.

If control module 102 decides not to end the iterative zeroing, the method may continue in either block (512) or block (510), depending on whether the selected zeroing capacitance, as modified by the capacitor connected in parallel, was greater than or less than the unselected zeroing capacitance in block (514). In the example of FIG. 12, the method 500 would continue in block (510), where capacitor 4C would be disconnected since 4C plus 8.9C is greater than 10C. Capacitor 2C would then be connected in parallel with $C_2$ in block (512).

After 4 iterations, control module 102 decides to end the iterative zeroing in either block (516) or block (518), when control module 102 has approximately zeroed the difference between $C_1$ and $C_2$. In other words, after 4 iterations, control module 102 has connected capacitors in parallel with the smaller of $C_1$ and $C_2$ such that the difference between $C_1$ and $C_2$ has been minimized. In the example of FIG. 12, a final instruction (e.g., 0001) of control module 102 would instruct zeroing capacitance module 138 to connect C to the selected zeroing capacitance ($C_2$) to form a capacitance of 9.9C. Accordingly, the difference between $C_1$ and $C_2$ with the zeroing capacitance of C connected to $C_2$ would be 0.1C. Since the iterative zeroing method 500 was performed in the absence of input, a capacitive difference in the absence of input may have been reduced from 1.1 C to 0.1 C. The iterative approximation method described above may then be performed while the connection of capacitor C is maintained by zeroing module 132 (520).

Figure 14:
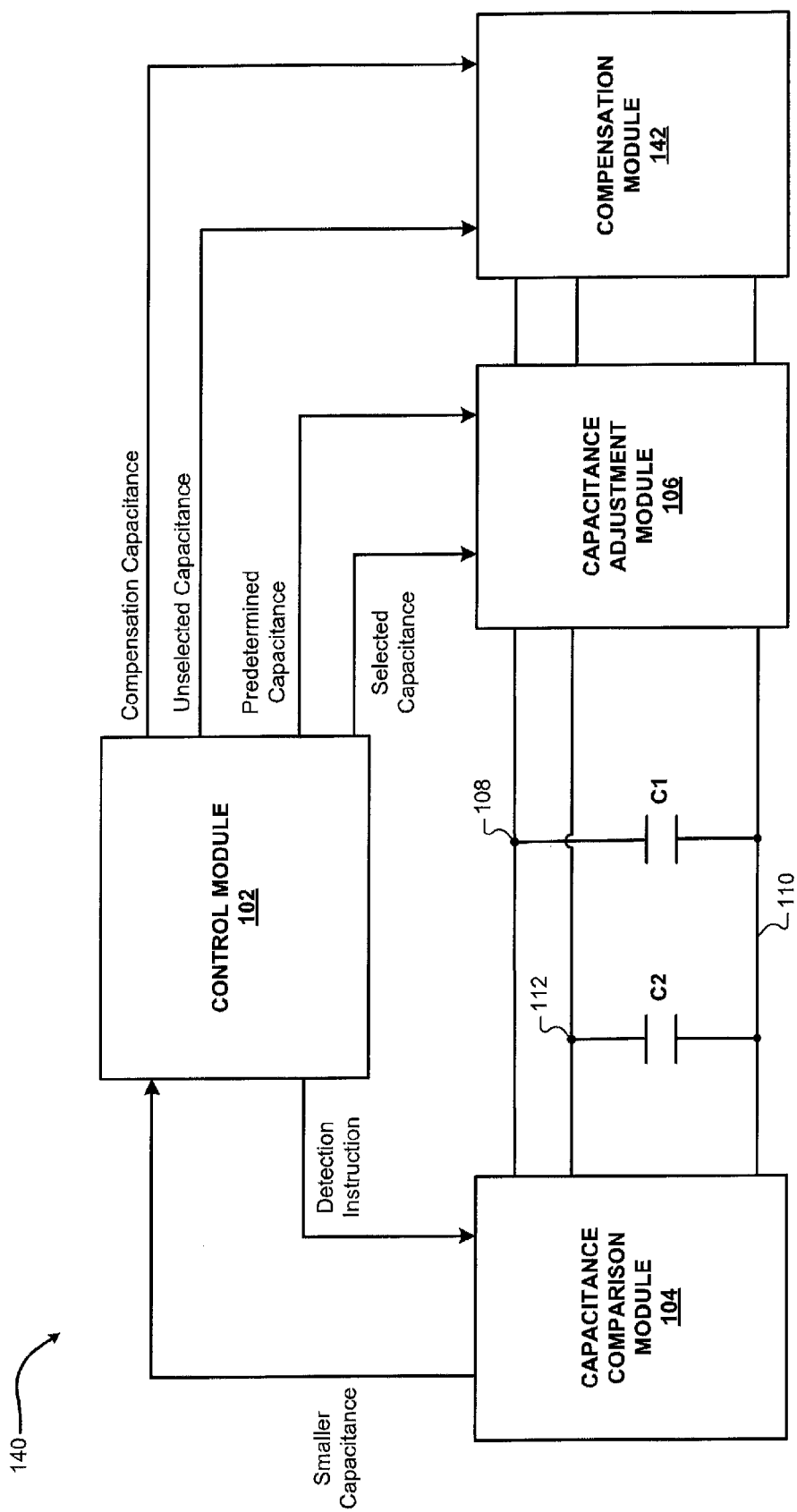
FIG. 14 is a functional block diagram of an example capacitance approximation system that includes a compensation module.

FIG. 14 illustrates a capacitance approximation system 140 that is similar to capacitance approximation system 100 except that capacitance approximation system 140 includes a compensation module 142. Compensation module 142 may adjust one of $C_1$ and $C_2$ in order to compensate, for example, for parasitic capacitances arising from switches of capacitance adjustment module 106. In some implementations, switches (e.g., $S_0$-$S_{N-1}$ of FIG. 7) of capacitance adjustment module 106 may give rise to parasitic capacitances that may add to the capacitors of capacitance adjustment module 106, and therefore add to the selected capacitance. For example, with respect to FIG. 7, switch $S_0$ may have an associated parasitic capacitance, such that when switch $S_0$ connects the capacitor having the value C to the selected capacitance, the total capacitance connected to the selected capacitance is modified by the parasitic capacitance associated with switch $S_0$. In some examples, switches of the present disclosure may include metal-oxide-semiconductor (MOS) transistors. Parasitic capacitances associated with the MOS transistors may include capacitances associated with the gate, bulk, drain, and source of the MOS transistors.

In order to compensate for the parasitic capacitances, e.g., associated with switches of capacitance adjustment module 106, compensation module 142 may add a capacitance to the unselected capacitance (i.e., a compensation capacitance) that is equal to the parasitic capacitance associated with capacitance adjustment module 106. For example, for each parasitic capacitance that may arise from a switch of capacitance adjustment module 106, compensation module 142 may include a similar capacitance that is equal in value. Compensation module 142 may add the similar capacitance to the unselected capacitance to balance the parasitic capacitance associated with capacitance adjustment module 106, so that a similar capacitance is added to both $C_1$ and $C_2$.

Figure 15:
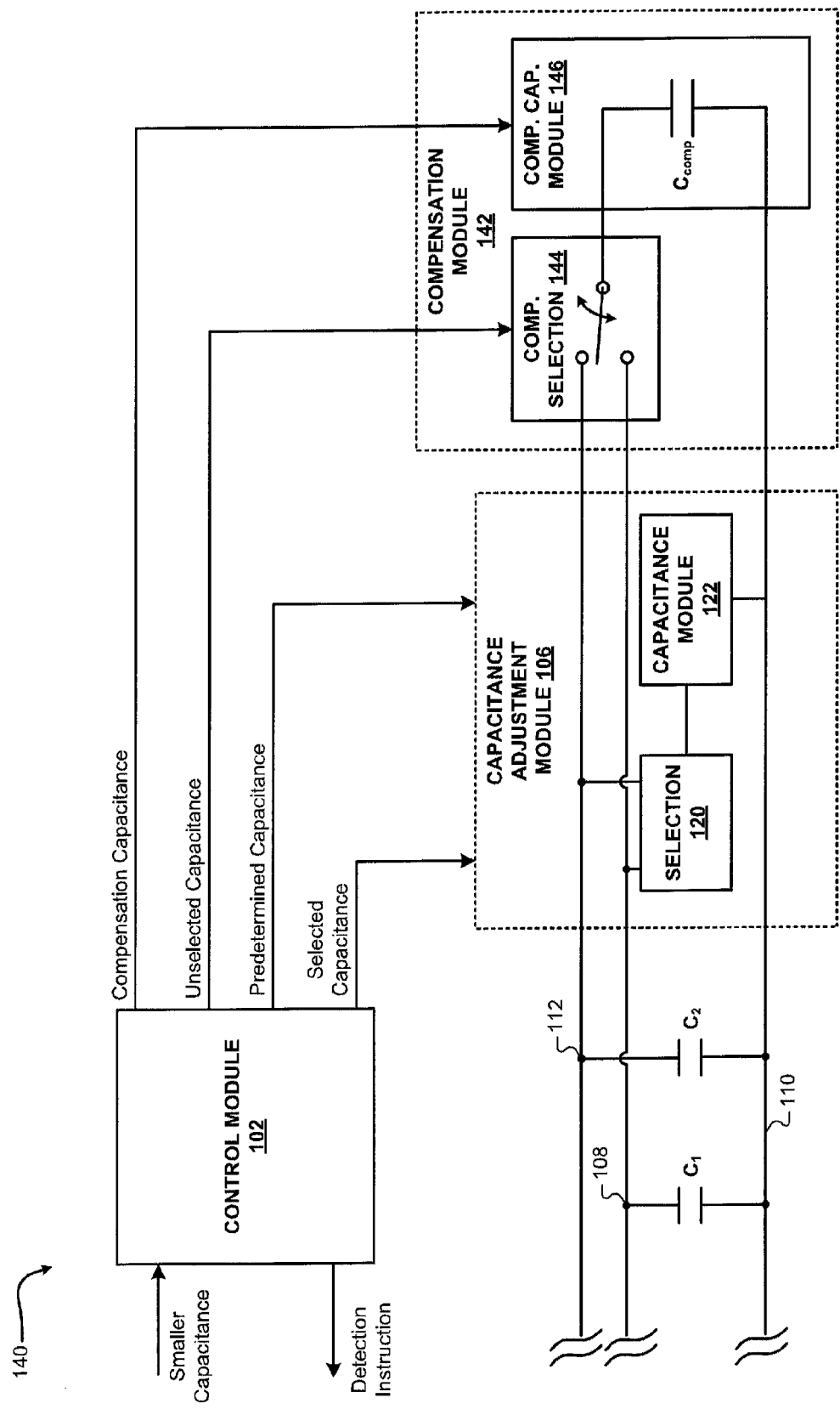
FIG. 15 illustrates a detailed view of an example compensation module of the capacitance approximation system of FIG. 14.

FIG. 15 illustrates an example compensation module 142. Compensation module 142 includes a compensation selection module 144 and a compensation capacitance module 146. Control module 102 instructs compensation selection module 144 to connect one of $C_1$ and $C_2$ to the compensation capacitance ($C_{comp}$) included in compensation capacitance module 146. $C_{comp}$ may be implemented using an array of predetermined capacitors, similar to capacitance module 122. Control module 102 may control compensation selection module 144 to connect $C_{comp}$ to the unselected capacitance so that $C_{comp}$ may provide compensation for parasitics arising from capacitance adjustment module 106. The instructions from control module 102 that control which of $C_1$ and $C_2$ are connected to $C_{comp}$, and the value of $C_{comp}$ are illustrated as "Unselected Capacitance" and "Compensation Capacitance," respectively.

As described above, capacitance module 122 may include parasitic capacitances for which compensation capacitance $C_{comp}$ may compensate. In one example, switches of capacitance module 122 that connect the N capacitors to the selected capacitance may give rise to parasitic capacitances when the switches are closed, i.e., connecting a capacitor to the selected capacitance. The parasitic capacitance arising from the closed switches may add to the selected capacitance, and therefore may affect the approximation of the difference between $C_1$ and $C_2$. In order to compensate for parasitics that may arise due to the switches of capacitance module 122, control module 102 may instruct compensation capacitance module 146 to connect a capacitance $C_{comp}$, that is equal to the parasitics, in parallel with the unselected capacitance. Accordingly, in some examples, each time a capacitor of capacitance module 122 is connected to the selected capacitance, which includes a parasitic capacitance, control module 102 may instruct compensation capacitance module 146 to connect an equivalent parasitic capacitance to the unselected capacitance in order to balance the amount of capacitance added to $C_1$ and $C_2$. In this manner, control module 102 may instruct compensation module 142 to compensate for parasitic capacitances that may arise during approximation.

Figure 16:
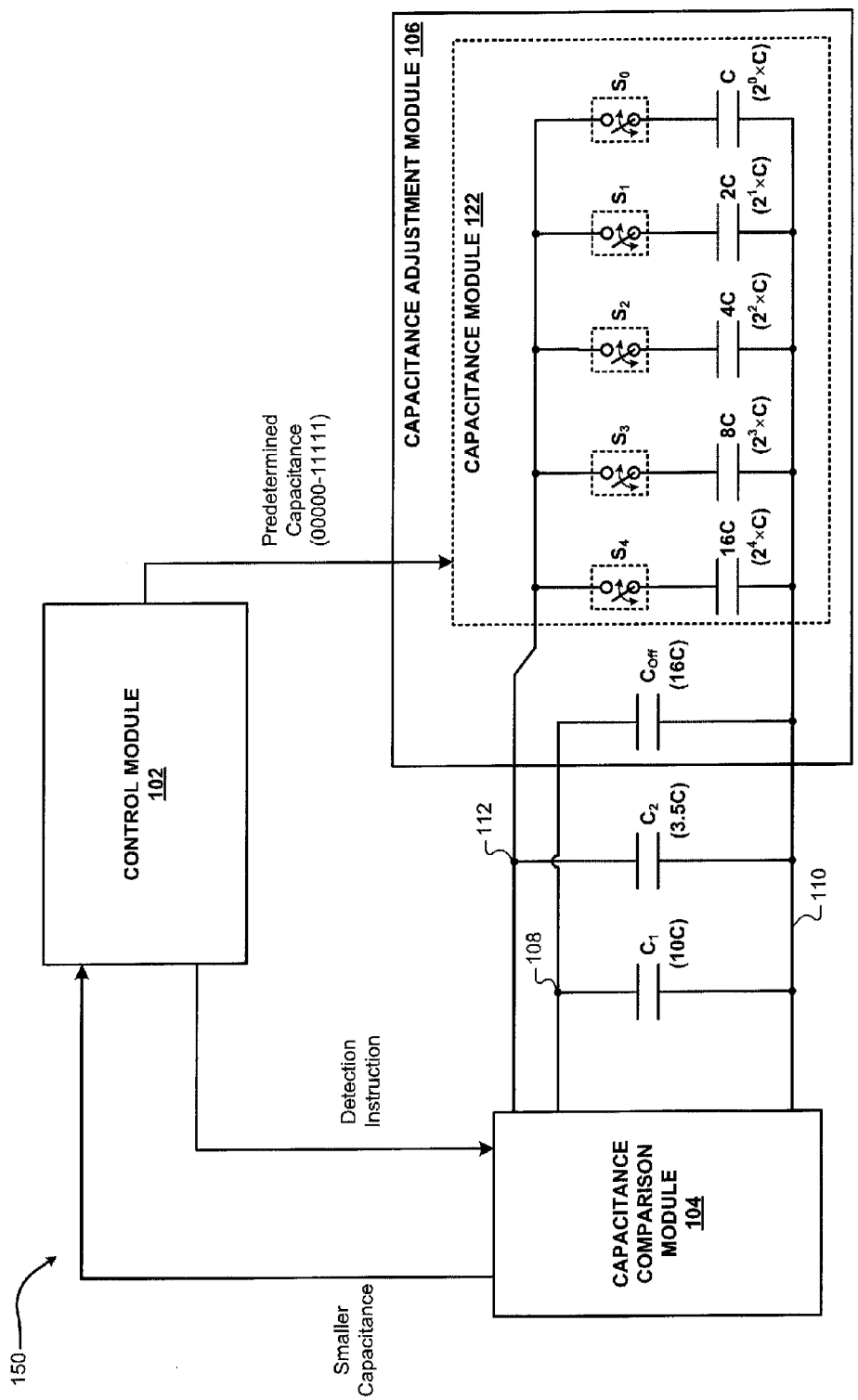
FIG. 16 is a functional block diagram of an example capacitance approximation system that includes an offset capacitor.

FIG. 16 shows an example capacitance approximation system 150 in which capacitance adjustment module 106 includes an offset capacitor "$C_{Off}$." $C_{Off}$ is connected to $C_1$ at the start of the iterative approximation method, and stays connected to $C_1$ during the iterative approximation method. Capacitance module 122 includes an additional capacitance (i.e., 16C) used to compensate for the addition of $C_{Off}$ during the iterative approximation method.

Capacitance $C_{Off}$ is selected such that $C_{Off}$ has a value that is greater than a difference that may be present between $C_1$ and $C_2$. Accordingly, regardless of the values of $C_1$ and $C_2$, the capacitance (either $C_1$ or $C_2$) to which $C_{Off}$ is connected will be greater than the capacitance (the other of $C_1$ or $C_2$) to which $C_{Off}$ is not connected. Since the connection of $C_{Off}$ to $C_1$ assures that $C_2$ will be the smaller capacitance when $C_{Off}$ is connected, capacitance approximation system 150 may eliminate the initial steps of the iterative approximation method in which the selected capacitance is determined. Instead, the iterative approximation method may begin by adding the largest capacitor (e.g., 16C) in parallel with $C_2$. Although $C_{Off}$ is illustrated as connected in parallel with $C_1$, in other examples, $C_{Off}$ may be connected in parallel with capacitance $C_2$ and the capacitance approximation system may selectively connect and disconnect capacitors from capacitance $C_1$.

The value of $C_{Off}$ is chosen such that adding it to either capacitance $C_1$ or $C_2$ will cause the combination of $C_{Off}$ and the capacitance to which it is added to be greater than the capacitance to which $C_{Off}$ is not added. For example, in the case where $C_1$ and $C_2$ are included in a capacitive accelerometer, the value of $C_{Off}$ may be chosen based on a maximum difference between capacitances $C_1$ and $C_2$ according to the specifications of the accelerometer.

Figure 18:
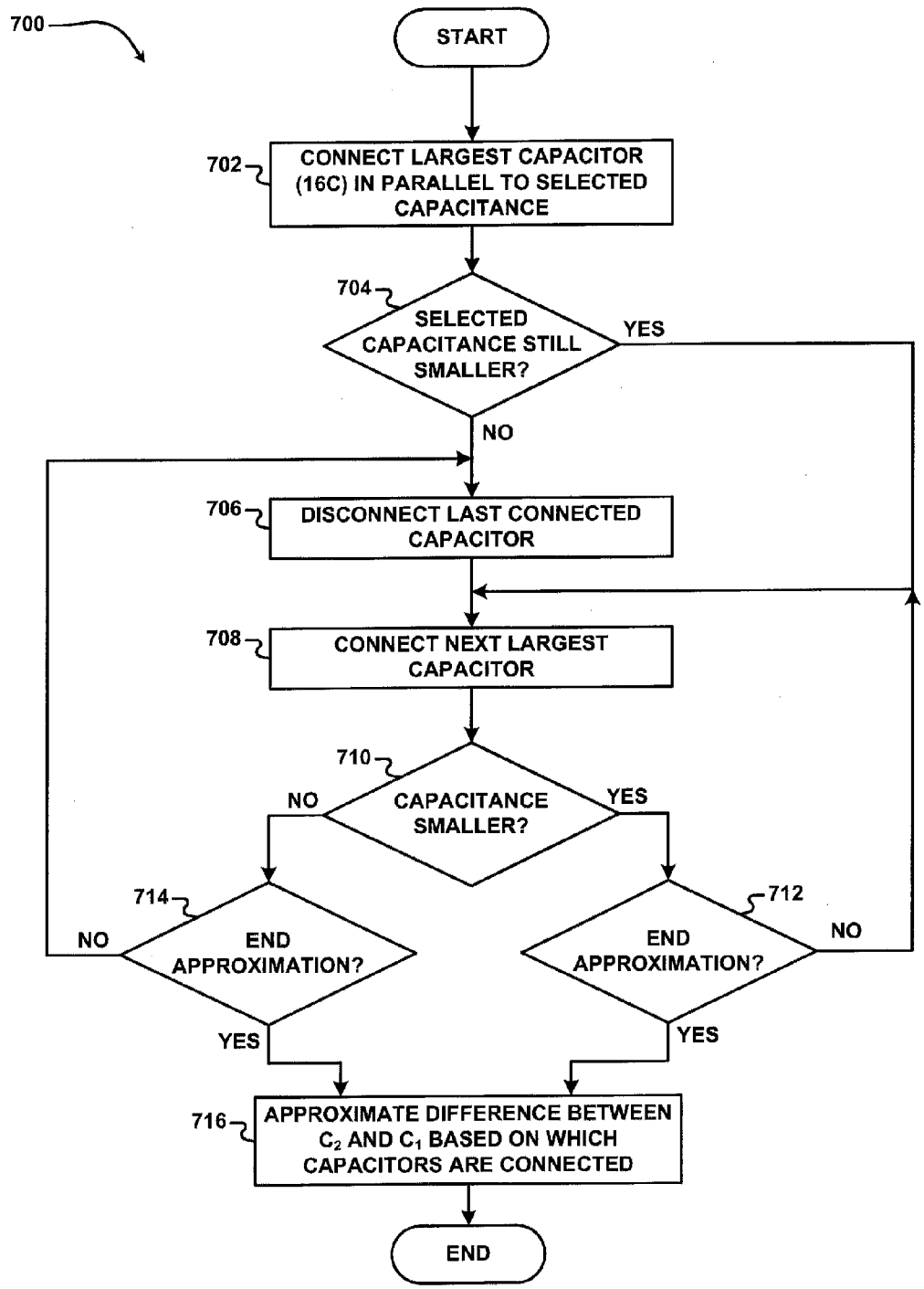
FIG. 18 illustrates an example iterative approximation method implemented using the example capacitance approximation system of FIG. 16.

Referring now to FIG. 18, an example iterative approximation method 700 implemented using an offset capacitor ($C_{Off}$) having a predetermined value is shown. Capacitance approximation system 150 of FIG. 16 and the table of FIG. 17 are referenced when describing method 700 in order to illustrate one example implementation of the method 700. The capacitance that is not connected to the offset capacitor $C_{Off}$ (i.e., $C_2$) during the method 700 may be referred to as the "selected capacitance."

Initially, control module 102 instructs capacitance module 122 to connect the largest capacitor of capacitance module 122 in parallel with the selected capacitance (702). For example, in FIG. 16, control module 102 would instruct capacitance module 122 to connect capacitor 16C in parallel with $C_2$. Control module 102 then instructs capacitance comparison module 104 to determine whether the selected capacitance in parallel with the largest capacitor is smaller than the unselected capacitance (704). For example, in FIG. 16, control module 102 would instruct capacitance comparison module 104 to determine whether $C_2$ in parallel with 16C is less than 26C. If comparison module 104 determines that the selected capacitance in parallel with the largest capacitor is larger than the unselected capacitance, capacitance module 122 disconnects the largest capacitor, in response to an instruction from control module 102 (706). If capacitance comparison module 104 determines that the selected capacitance in parallel with the largest capacitor is smaller, capacitance module 122 connects the next largest capacitor in parallel with the selected capacitance (708). In the example of FIG. 16, the largest capacitance (i.e., 16C) would remain connected to $C_2$ while the next largest capacitance (i.e., 8C) was connected to $C_2$ to form a capacitance of 27.5C.

Capacitance comparison module 104 then compares the relative magnitude of the selected capacitance with the unselected capacitance after connection of the next largest capacitance (710). In the example of FIG. 16, capacitance comparison module 104 compared capacitance $C_1$ to capacitance $C_2$ in parallel with 24C. If capacitance comparison module 104 determines that the selected capacitance is smaller than the unselected capacitance, control module 102 determines whether to end the iterative approximation in block (712). If capacitance comparison module 104 determines that the selected capacitance is not smaller than the unselected capacitance, control module 102 determines whether to end the iterative approximation in block (714). For example, control module 102 may determine whether to end the iterative approximation in blocks (712) or (714) based on whether a predetermined number of iterations have been performed. In the example of FIG. 16, the predetermined number of iterations may be equal to the number of iterations required to connect and compare each of the capacitors of capacitance module 122.

If control module 102 decides not to end the iterative approximation, the method 700 may continue in either block (706) or block (708), depending on whether the selected capacitance, as modified by the capacitor connected in parallel, was greater than or less than the unselected capacitance in block (710). In the example of FIG. 16, the method 700 would continue in block (706), where capacitor 4C would be connected in parallel with $C_2$ and 16C.

If control module 102 decides to end the iterative approximation in either block (712) or block (714), control module 102 approximates the difference between $C_2$ and $C_1$ (716). Control module 102 may determine $\Delta C_{approx}$ based on the final instruction (e.g., binary instruction) set to control capacitance module 122. In the example of FIG. 16, since a final instruction (e.g., 10110) of control module 102 instructed capacitance module 122 to connect 4C and 2C to the selected capacitance, control module 102 may determine that $\Delta C_{approx}$ is equal to 6C. Stated another way, control module 102 may approximate $\Delta C$ based on which capacitors are connected to the selected capacitance after the predetermined number of iterations. The most significant bit (i.e., the bit corresponding to 16C) may serve as a sign bit that indicates which of $C_1$ and $C_2$ is larger. When the most significant bit is set to 1, as in FIG. 16, it indicates that the capacitance connected to $C_{Off}$ is larger than the capacitance not connected to $C_{Off}$.

Figure 19:
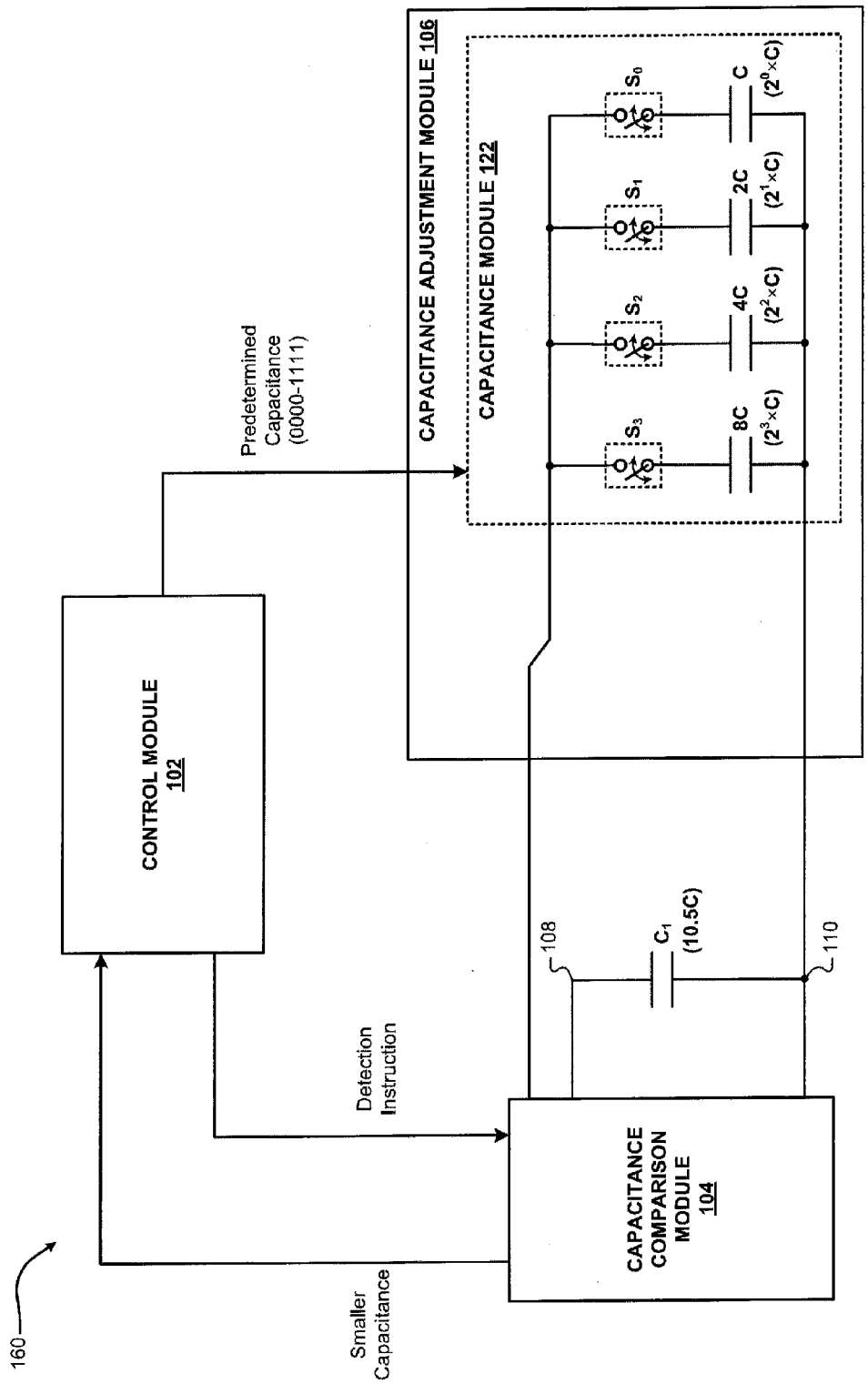
FIG. 19 is a functional block diagram of an example capacitance approximation system that approximates the value of a target capacitance.
Figure 21:
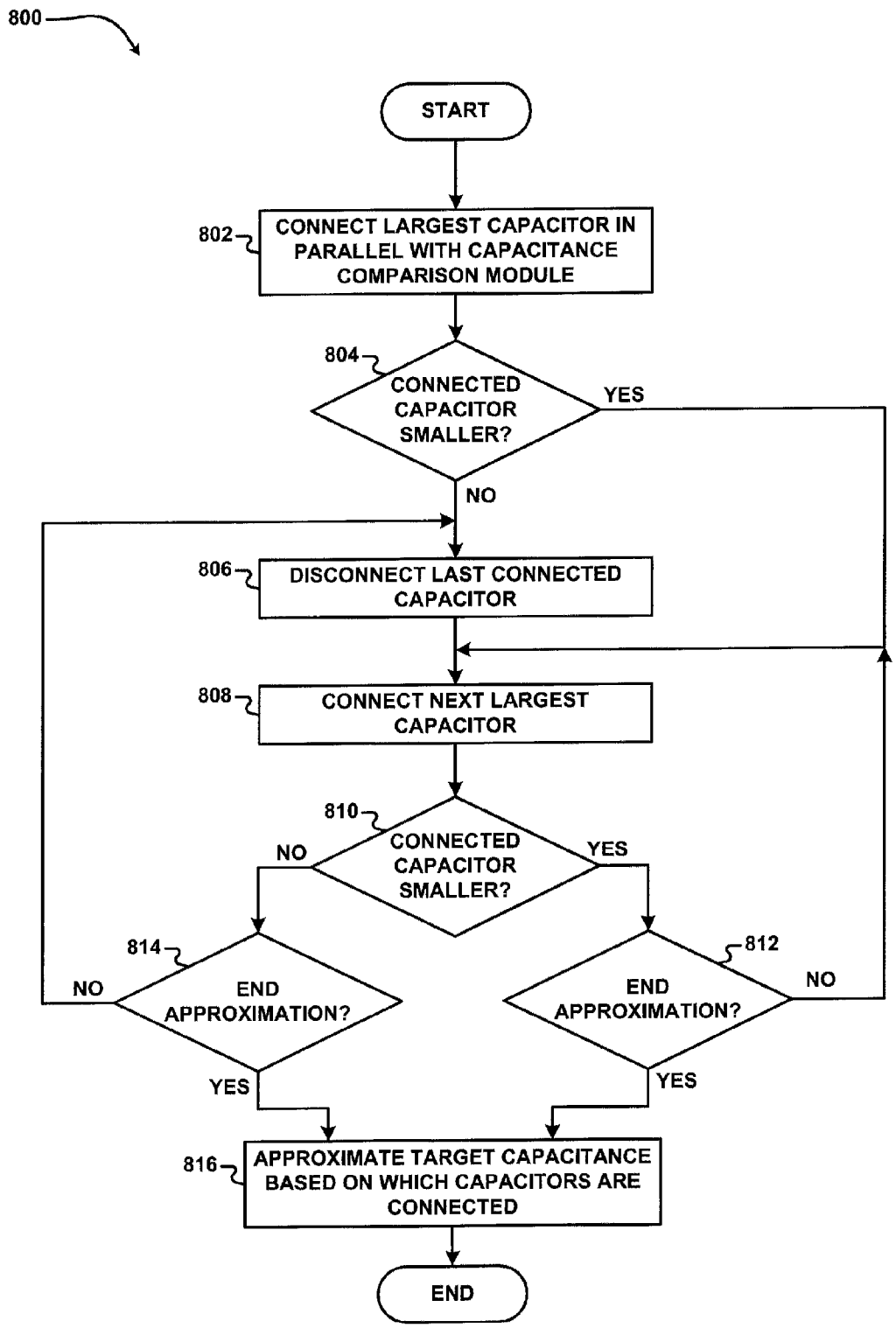
FIG. 21 illustrates an example iterative approximation method implemented using the example capacitance approximation system of FIG. 19.

Referring now to FIG. 19, an example capacitance approximation system 160 may approximate the capacitance of a single capacitance ($C_1$), referred to hereinafter as a "target capacitance." FIG. 21 shows an example iterative approximation method 800 that approximates a capacitance of a single capacitance. Capacitance approximation system 160 of FIG. 19 and the table of FIG. 20 are referenced when describing method 800 in order to illustrate one example implementation of the method 800.

Initially, control module 102 instructs capacitance module 122 to connect the largest capacitor of capacitance module 122 in parallel with capacitance comparison module 104 (802). For example, in FIG. 19, control module 102 would instruct capacitance module 122 to connect capacitor 8C in parallel with capacitance comparison module 104. Control module 102 then instructs capacitance comparison module 104 to determine whether the connected capacitance (e.g., 8C) is smaller than the target capacitance $C_1$. For example, in FIG. 19, control module 102 would instruct capacitance comparison module 104 to determine whether 8C is less than 10.5C. If comparison module 104 determines that the connected capacitor is larger than the target capacitance, capacitance module 122 disconnects the connected capacitor, in response to an instruction from control module 102 (806). If capacitance comparison module 104 determines that the connected capacitance is smaller than the target capacitance, capacitance module 122 connects the next largest capacitor (e.g., 4C) in parallel with the capacitance comparison module 104 (808). In the example of FIG. 19, the largest capacitance (i.e., 8C) was not disconnected and the next largest capacitance (i.e., 4C) was connected according to blocks (806) and (808).

Capacitance comparison module 104 then compares the relative magnitude of the connected capacitors and the target capacitance (810). If capacitance comparison module 104 determines that the connected capacitor is smaller than the target capacitance, control module 102 determines whether to end the iterative approximation in block (812). If capacitance comparison module 104 determines that the connected capacitor is not smaller than the target capacitance, control module 102 determines whether to end the iterative approximation in block (814). For example, control module 102 may determine whether to end the iterative approximation in blocks (812) or (814) based on whether a predetermined number of iterations have been performed.

If control module 102 decides to end the iterative approximation in either block (812) or block (814), control module 102 approximates the target capacitance (816). Control module 102 may approximate the target capacitance based on the final instruction (e.g., binary instruction) set to control capacitance module 122. In the example of FIG. 19, since a final instruction (e.g., 1010) of control module 102 instructed capacitance module 122 to connect 8C and 2C to capacitance comparison module 104, control module 102 may determine that the target capacitance is approximately equal to 10C.

Although not illustrated in FIG. 19, in some examples, capacitance adjustment module 106 may include a capacitor having a predetermined value added in parallel with the nodes of capacitance module 122 in order to adjust a range of capacitance that may be determined by capacitance approximation system 160. In practice, $C_1$ may have a value that is larger than the sum of the capacitors included in capacitance module 122. When this is the case, a predetermined capacitor having a value slightly less than $C_1$ and added in parallel with capacitance module 122 may allow the capacitance approximation system 160 to determine the value of capacitance $C_1$. For example, when the predetermined capacitor is added in parallel with capacitance module 122, the resulting capacitance determined by the iterative approximation method may be added to the predetermined capacitance to determine the value of the target capacitance $C_1$.

Figure 22:
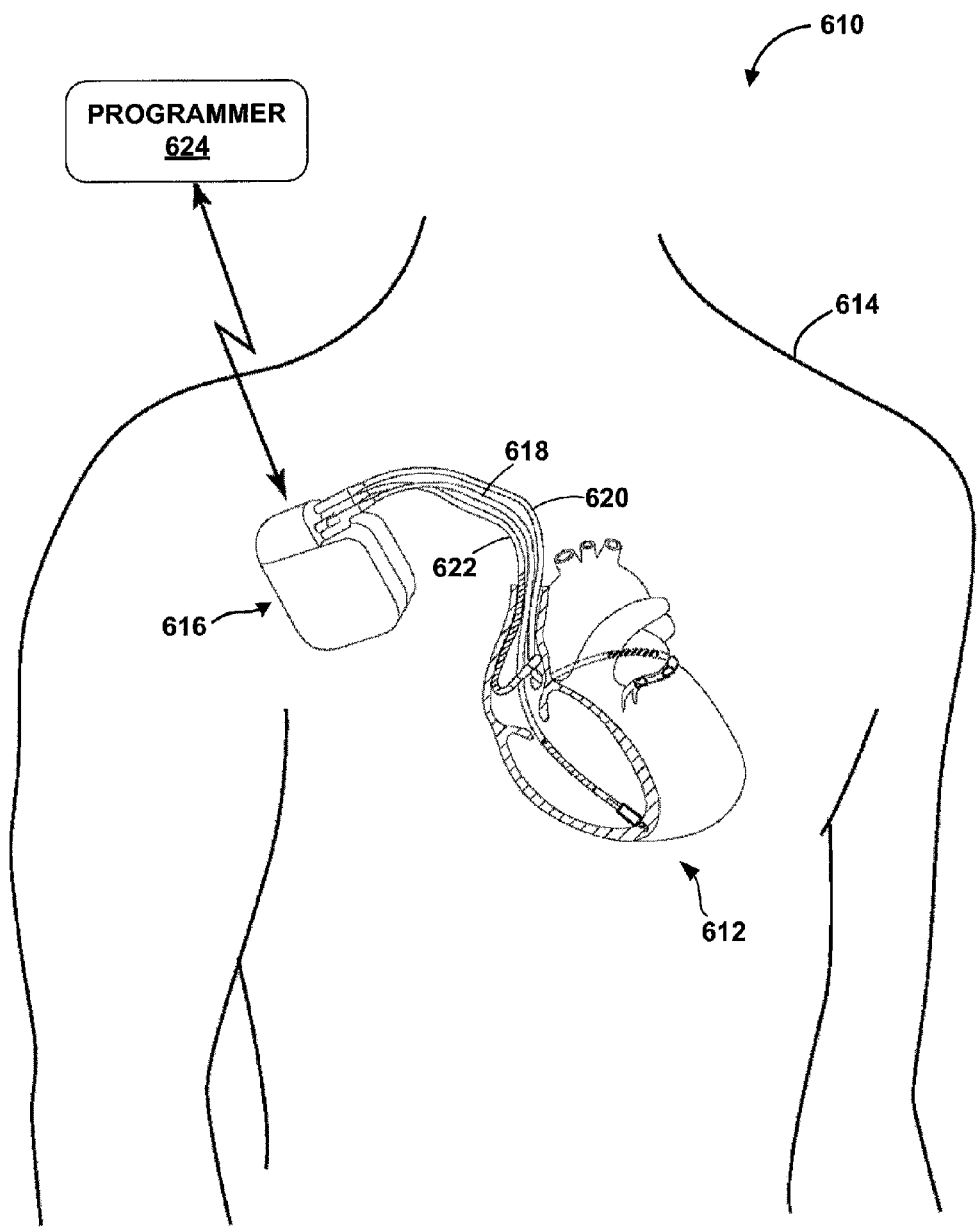
FIG. 22 is a functional block diagram that illustrates an example implementation of the capacitance approximation system in a medical device system.

FIG. 22 is a conceptual diagram of an example medical device system 610 that may be used to provide therapy to heart 612 of patient 614. System 610 includes an IMD 616, which is coupled to leads 618, 620, and 622. For example, IMD 616 may be an implantable pacemaker, cardioverter, and/or defibrillator that provides electrical signals to heart 612 using one or more of leads 618, 620, 622. Leads 618, 620, 622 extend into heart 612 of patient 614. Leads 618, 620, 622 sense electrical activity of heart 612 and/or deliver electrical stimulation to heart 612. In some examples, IMD 616 may implement capacitance approximation system 100, 130, 140 of the present disclosure as described hereinafter.

System 610 includes a programmer 624 that communicates wirelessly with IMD 616. Programmer 624 may be a handheld computing device, a desktop computing device, a networked computing device, etc. Programmer 624 may retrieve data stored in IMD 616 and/or program IMD 616 to provide various therapies. Accordingly, a user may retrieve data from IMD 616 and program IMD 616 using programmer 624. IMD 616 and programmer 624 may communicate via wireless communication using any techniques known in the art.

Figure 23:
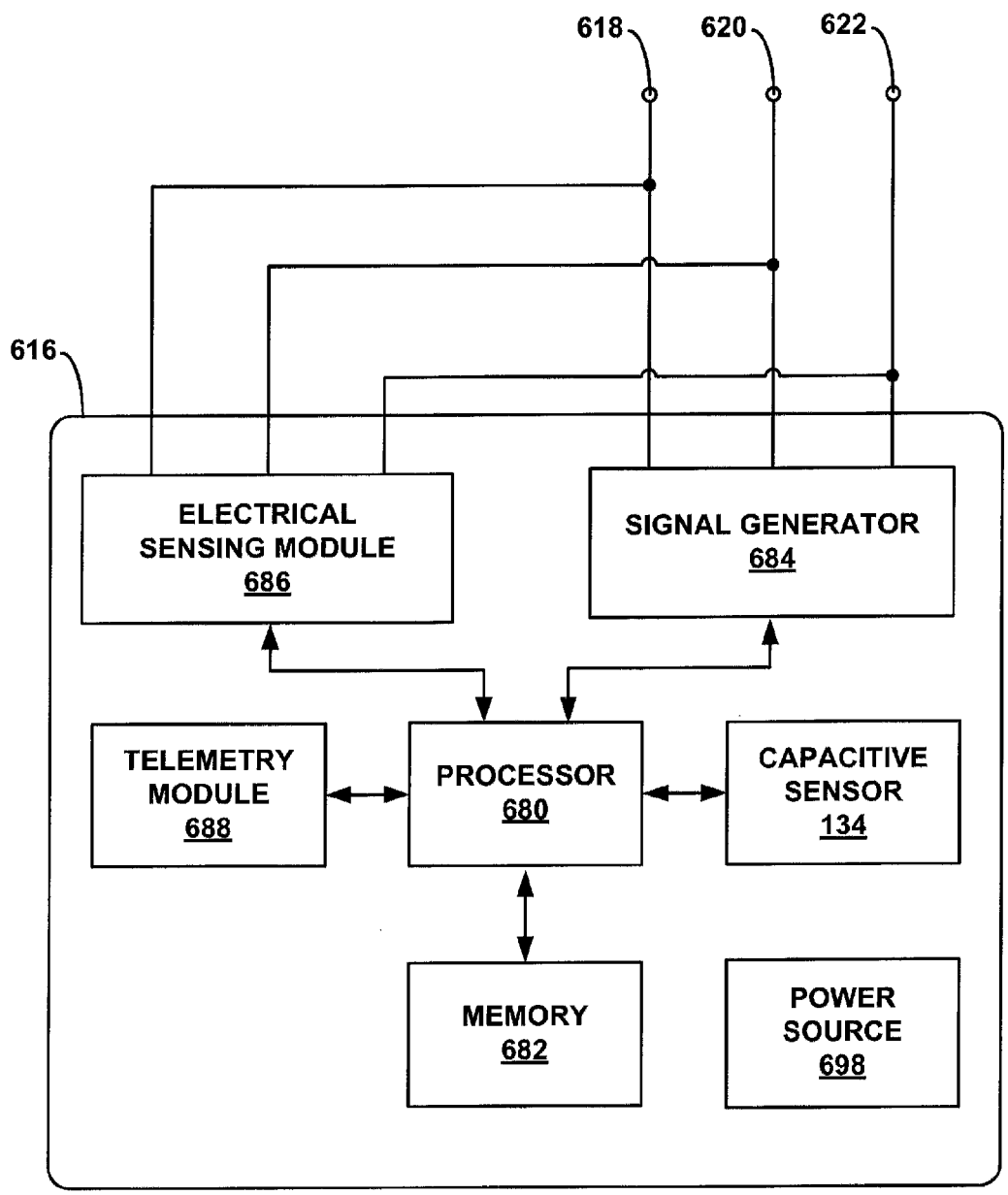
FIG. 23 is a functional block diagram that illustrates an example configuration of an implantable medical device that includes the capacitance approximation system.

FIG. 23 is a functional block diagram that illustrates an example configuration of IMD 616. IMD 616 includes a processor 680, memory 682, a signal generator 684, an electrical sensing module 686, a telemetry module 688, a power source 698, and capacitive sensor 134. Memory 682 may include computer-readable instructions that, when executed by processor 680, cause IMD 616 and processor 680 to perform various functions attributed to IMD 616 and processor 680 herein. Memory 682 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other digital media.

Processor 680 may include any one or more of a microprocessor, a microcontroller, a digital signal processor (DSP), an application specific integrated circuit (ASIC), a field-programmable gate array (FPGA), or equivalent discrete or integrated logic circuitry. In some examples, processor 680 may include multiple components, such as any combination of one or more microprocessors, one or more microcontrollers, one or more DSPs, one or more ASICs, or one or more FPGAs, as well as other discrete or integrated logic circuitry. The functions attributed to processor 680 herein may be embodied as software, firmware, hardware or any combination thereof. Processor 680 may include capacitance approximation system 100, 130, 140 of the present disclosure. For example, processor 680 may include control module 102, capacitance comparison module 104, and capacitance adjustment module 106.

Signal generator 684 is electrically coupled to electrodes on leads 618, 620, 622. Signal generator 684 is configured to generate and deliver electrical stimulation therapy to heart 612 via the electrodes on leads 618, 620, 622. For example, signal generator 684 may deliver pacing pulses and/or defibrillation shocks to heart 612. Processor 680 controls signal generator 684 to deliver stimulation therapy to heart 612.

Electrical sensing module 686 monitors signals from electrodes of leads 618, 620, 622. Processor 680 monitors electrical activity of heart 612 based on data received from electrical sensing module 686. Processor 680 may store cardiac EGMs, marker channel data, and so on, for physiological episodes, such as tachyarrhythmias, within memory 682.

Telemetry module 688 includes any suitable hardware, firmware, software or any combination thereof for communicating with another device, such as programmer 624. Under control of processor 680, telemetry module 688 may receive downlink telemetry from and send uplink telemetry to programmer 624 with the aid of an antenna (not shown), which may be internal and/or external. The various components of IMD 616 are coupled to a power source 698, which may include a rechargeable or non-rechargeable battery.

Although illustrated as a component of IMD 616, capacitive sensor 134 may be positioned in various locations in system 610. For example, capacitive sensor 134 may be located within IMD 616, outside of IMD 616, or on or within one or more of leads 618, 620, 622. In some implementations, capacitive sensor 134 may be external (i.e., not implanted).

Capacitive sensor 134 may comprise a capacitive accelerometer as described above. Accordingly, capacitive sensor 134 may detect various physical parameters associated with patient 614. The various parameters may include physical activity associated with patient 614, e.g., contraction of the heart 612, activity of patient 614, posture of patient 614, and respiration of patient 614. Processor 680 may include capacitive approximation system 100 and may implement the iterative approximation method to approximate the various parameters indicated by capacitive sensor 134. Processor 680 may then store the approximated parameters in memory 682 and/or transmit the approximated parameters to programmer 624 via telemetry module 688, for example.

Various examples have been described. These and other examples are within the scope of the following claims.

The invention claimed is:

1. A system comprising:
    a capacitance adjustment module configured to connect one or more of N capacitors in parallel with one of a first and second capacitance;
    a capacitance comparison module configured to determine which of the first and second capacitances is smaller; and
    a control module configured to identify the smaller capacitance and the larger capacitance of the first and second capacitances based on the determination made by the capacitance comparison module, and subsequently, during each of M iterations:
    instruct the capacitance adjustment module to connect at least one of the N capacitors across a set of nodes in parallel with the smaller identified capacitance; and
    determine whether the capacitance associated with the set of nodes is greater than the larger identified capacitance,
    wherein, after the M iterations, the control module is configured to approximate a difference between the first and second capacitances based on as being equal to a sum of the N capacitors that are connected across the set of nodes, where M is an integer greater than or equal to 1, and N is an integer greater than or equal to 2.

2. The system of claim 1, wherein the control module is configured to instruct the capacitance adjustment module to connect a different combination of the N capacitors during each of the M iterations.

3. The system of claim 1, wherein the control module, during each of the M iterations, is configured to instruct the capacitance adjustment module to disconnect the at least one of the N capacitors when the capacitance associated with the set of nodes is greater than the larger identified capacitance.

4. The system of claim 1, wherein the N capacitors have binary-weighted values.

5. The system of claim 1, wherein the capacitance comparison module is configured to deliver current to the first and second capacitances and determine which of the first and second capacitances is smaller.

6. The system of claim 5, wherein the capacitance comparison module configured to determine which of the first and second capacitances is smaller based on which of the first and second capacitances develops voltage at a higher rate in response to the current.

7. The system of claim 6, wherein the control module is configured to identify the smaller and larger of the first and second capacitances based on which of the first and second capacitances develops voltage at a higher rate.

8. The system of claim 1, wherein the control module is configured to instruct the capacitance adjustment module using a binary value that indicates which of the one or more of the N capacitors to connect.

9. The system of claim 8, wherein each bit of the binary value corresponds to one of the N capacitors.

10. The system of claim 1, wherein the control module is configured to instruct the capacitance adjustment module using a binary value that indicates which of the one or more of the N capacitors to disconnect.

11. The system of claim 1, wherein the control module is configured to instruct the capacitance adjustment module to connect the one of the N capacitors across the set of nodes using a binary value that indicates the set of nodes.

12. The system of claim 1, wherein the capacitance comparison module is configured to:
    deliver current to the larger identified capacitance and the capacitance associated with the set of nodes; and
    determine when the capacitance associated with the set of nodes is greater than the larger identified capacitance based on which of the larger identified capacitance and the capacitance associated with the set of nodes develops voltage at a higher rate.

13. The system of claim 12, wherein the control module is configured to determine whether the capacitance associated with the set of nodes is greater than the larger identified capacitance based on which of the larger identified capacitance and the capacitance associated with the set of nodes develops voltage at a higher rate.

14. The system of claim 1, wherein N is equal to M.

15. The system of claim 1, wherein the first and second capacitances are included in an accelerometer, and wherein the control module is configured to determine an approximate acceleration of the accelerometer based on the approximated difference between the first and second capacitances.

16. The system of claim 15, further comprising a zeroing capacitance module configured to add capacitors to one of the first and second capacitances, wherein the control module is configured to instruct the zeroing capacitance module to add capacitors to one of the first and second capacitances such that a difference between the first and second capacitances is decreased when the accelerometer is not subject to acceleration.

17. The system of claim 1, further comprising a capacitance compensation module configured to add capacitors to the larger identified capacitance such that the added capacitors are equal to parasitic capacitances associated with the capacitors connected in parallel with the smaller identified capacitance.

18. The system of claim 1, wherein the sum is a first sum, and wherein, after the M iterations, the control module is configured to determine that the approximate difference between the first and second capacitances is equal to a second sum of the capacitors connected across the set of nodes.

19. A method comprising:
    determining, by a capacitance comparison module, which of a first capacitance and a second capacitance is smaller;
    identifying, by a control module, the smaller capacitance and the larger capacitance of the first and second capacitances based on the determination of which of the first and second capacitances is smaller;

during each of M iterations:
controlling, by the control module, a connection of at least one of N capacitors across a set of nodes in parallel with the smaller identified capacitance; and
determining, by the control module, whether the capacitance associated with the set of nodes is greater than the larger identified capacitance; and
after the M iterations, approximating, by the control module, a difference between the first and second capacitances as being equal to a sum of the N capacitors that are connected across the set of nodes, where M is an integer greater than or equal to 1, and N is an integer greater than or equal to 2.

20. The method of claim 19, further comprising controlling, by the control module, a connection of a different combination of the N capacitors during each of the M iterations.

21. The method of claim 19, further comprising, during each of the M iterations, controlling, by the control module, a disconnection of the at least one of the N capacitors when the capacitance associated with the set of nodes is greater than the larger identified capacitance.

22. The method of claim 19, wherein the N capacitors have binary-weighted values.

23. The method of claim 19, wherein N is equal to M.

24. The method of claim 19, wherein the sum is a first sum, the method further comprising, after the M iterations, determining, by the control module, that the approximate difference between the first and second capacitances is equal to a second sum of the capacitors connected across the set of nodes.

25. The method of claim 19, further comprising:
delivering, by the control module, current to the first and second capacitances; and
determining, by the control module, which of the first and second capacitances is smaller based on which of the first and second capacitances develops voltage at a higher rate in response to the current.

26. The method of claim 19, further comprising controlling, by the control module one of a connection of or a disconnection of the at least one of the N capacitors using a binary value that indicates which of the N capacitors to connect or disconnect, wherein each bit of the binary value corresponds to one of the N capacitors.

27. The method of claim 19, further comprising controlling, by the control module, a connection of the one of the N capacitors across the set of nodes using a binary value that indicates the set of nodes.

28. A system comprising:
means for determining which of a first and second capacitance is smaller;
means for identifying the smaller capacitance and the larger capacitance of the first and second capacitances based on the determination of which of the first and second capacitances is smaller;
means for, during each of M iterations:
connecting at least one of N capacitors across a set of nodes in parallel with the smaller identified capacitance; and
determining whether the capacitance associated with the set of nodes is greater than the larger identified capacitance; and
means for, after the M iterations, approximating a difference between the first and second capacitances as being equal to a sum of the N capacitors that are connected across the set of nodes, where M and N are integers greater than or equal to 1.

29. The system of claim 28, further comprising means for connecting a different combination of the N capacitors during each of the M iterations.

30. The system of claim 28, further comprising means for, during each of the M iterations, disconnecting the at least one of the N capacitors when the capacitance associated with the set of nodes is greater than the larger identified capacitance.

31. The system of claim 28, wherein the N capacitors have binary-weighted values.

32. The system of claim 28, wherein N is equal to M.

33. The system of claim 28, wherein the sum is a first sum, the system further comprising, after the M iterations, means for determining that the approximate difference between the first and second capacitances is equal to a second sum of the capacitors connected across the set of nodes.

34. The system of claim 28, further comprising:
means for delivering current to the first and second capacitances; and
means for determining which of the first and second capacitances is smaller based on which of the first and second capacitances develops voltage at a higher rate in response to the current.

35. The system of claim 28, further comprising means for one of connecting or disconnecting the at least one of the N capacitors using a binary value that indicates which of the N capacitors to connect or disconnect, wherein each bit of the binary value corresponds to one of the N capacitors.

36. A system comprising:
a capacitance adjustment module configured to connect one or more of N capacitors in parallel with a first capacitance and configured to connect an offset capacitor having a predetermined value in parallel with a second capacitance; and
a control module configured to, during each of M iterations:
instruct the capacitance adjustment module to connect at least one of the N capacitors across a set of nodes in parallel with the first capacitance; and
determine whether the capacitance associated with the set of nodes is greater than the offset capacitor in parallel with the second capacitance,
wherein, after the M iterations, the control module is configured to approximate the difference between the first and second capacitances as being equal to a sum of the N capacitors that are connected across the set of nodes, where M is an integer greater than or equal to 1, and N is an integer greater than or equal to 2.

37. The system of claim 36, wherein the control module is configured to instruct the capacitance adjustment module to connect a different combination of the N capacitors during each of the M iterations.

38. The system of claim 36, wherein the control module, during each of the M iterations, is configured to instruct the capacitance adjustment module to disconnect the at least one of the N capacitors when the capacitance associated with the set of nodes is greater than the offset capacitor in parallel with the second capacitance.

39. The system of claim 36, wherein the N capacitors include at least one capacitor having a value that is equal to the value of the offset capacitor.

40. The system of claim 36, wherein the value of the offset capacitor is selected such that the value of the offset capacitor is greater than or equal to a maximum difference between the first and second capacitances.

41. The system of claim 36, wherein the first and second capacitances are included in a sensor, and wherein the control module is configured to approximate a parameter measured by the sensor based on the difference between the first and second capacitances.

42. A system comprising:
- a capacitance adjustment module configured to connect one or more of N capacitors across a set of nodes;
- a capacitance comparison module configured to:
  - connect to the set of nodes;
  - connect to a target capacitance; and
  - determine which of the target capacitance and a capacitance associated with the set of nodes is larger; and
- a control module configured to, during each of M iterations:
  - instruct the capacitance adjustment module to connect at least one of the N capacitors across the set of nodes; and
  - instruct the capacitance comparison module to determine which of the target capacitance and the capacitance associated with the set of nodes is larger,
- wherein, after the M iterations, the control module is configured to approximate the target capacitance as being equal to a sum of the N capacitors that are connected across the set of nodes, where M is an integer greater than or equal to 1, and N is an integer greater than or equal to 2.

43. The system of claim 42, wherein the control module is configured to instruct the capacitance adjustment module to connect a different combination of the N capacitors during each of the M iterations.

44. The system of claim 42, wherein the control module, during each of the M iterations, is configured to instruct the capacitance adjustment module to disconnect the at least one of the N capacitors when the capacitance associated with the set of nodes is larger than the target capacitance.

* * * * *